United States Patent [19]
Godowski

[11] Patent Number: 5,770,704
[45] Date of Patent: Jun. 23, 1998

[54] RECEPTOR ACTIVATION WITH INACTIVE HEPATOCYTE GROWTH FACTOR LIGANDS

[75] Inventor: Paul J. Godowski, Pacifica, Calif.

[73] Assignee: Genentech, Inc., South San Francisco, Calif.

[21] Appl. No.: 792,078

[22] Filed: Jan. 31, 1997

Related U.S. Application Data

[60] Continuation of Ser. No. 423,291, Apr. 17, 1995, abandoned, which is a division of Ser. No. 268,880, Jun. 30, 1994, abandoned, which is a continuation of Ser. No. 950,572, Sep. 22, 1992, abandoned, which is a continuation-in-part of Ser. No. 884,811, May 18, 1992, Pat. No. 5,316,921, and Ser. No. 885,971, May 18, 1992, Pat. No. 5,328,837.

[51] Int. Cl.$^6$ .......................... A61K 38/18; C07K 14/475
[52] U.S. Cl. ................. 530/402; 424/194.1; 424/195.11; 530/399
[58] Field of Search .................................. 530/402, 399, 530/350; 424/194.1, 195.11, 185.1, 198.1

[56] References Cited

U.S. PATENT DOCUMENTS

| | | | |
|---|---|---|---|
| 4,931,548 | 6/1990 | Lucas et al. | 530/399 |
| 4,935,233 | 6/1990 | Bell et al. | 424/85.5 |
| 5,100,788 | 3/1992 | Lofdahl et al. | 435/69.7 |
| 5,108,910 | 4/1992 | Curtis et al. | 435/69.7 |
| 5,227,158 | 7/1993 | Jardieu | 424/85.5 |
| 5,334,532 | 8/1994 | Tackney et al. | 435/252.33 |

FOREIGN PATENT DOCUMENTS

| | | |
|---|---|---|
| 225579 | 6/1987 | European Pat. Off. . |
| WO 90/04788 | 5/1990 | WIPO . |
| WO 90/15142 | 12/1990 | WIPO . |
| WO 91/05853 | 5/1991 | WIPO . |

OTHER PUBLICATIONS

Ashkenazi et al., "Protection Against Endotoxic Shock by a Tumor Necrosis Factor Receptor Immunoadhesion" *Proc. Natl. Acad. Sci.* 88:10535–10539 (1991).

Ashkenazi, et al., "Comparative Study of in Vitro and in Vivo Modulation of Lactogenic and Somatotropic Receptors by Native Human Growth Hormone and Its Modified Analog Prepared by Recombinant Deoxyribonucleic Acid Technology" *Endocrinology* 121(1):414–419 (1987.

Becker et al., "Chemical physical, and biological characterization of a dimeric form of biosynthetic human growth hormone" *Biotechnology and Applied Biochemistry* 9:478–487 (1987).

Binder et al, "Site–directed mutations of human growth hormone that selectively modify its lactogenic activity and binding properties" *Molecular Endocrinolgy* 4(7):1060–1068 (1990).

Bottaro et al., "Identification of the Hepatocyte Growth Factor Receptor as the c–met Proto–Oncogene Product" *Science* 251:802–804 (Feb. 15, 1991

Chan et al., "Glycine 119 of Bovine Growth Hormone is Critical for Growth–Promoting Activity" *Molecular Endocrinology* 5:1845 (1991).

Cunningham et al., "High–Resolution Epitope Mapping of hGH–Receptor Interactions by Alanine–Scanning Mutagenesis" *Science* 244:1081–1085 (1989).

Cunningham et al., "Receptor and Antibody Epitopes n Human Growth Hormone Identified by Homolog–Scanning Mutagenesis" *Science* 243:1330–1336 (1989).

Cunningham et al., "Dimerization of the Extracellular Domain of the Human Growth Hormone Receptor by a Single Hormone Molecule" *Science* 254:821–825 (1991).

Engelman et al., "Antibodies to a soluble form of a tumor necrosis factor (TNF) receptor have TNF–like activity" *Journal of Biological Chemistry* 265:14497–14504 (1990).

Gertler et al., "Inhibition of Lactogenic Activities of Ovine Prolactin and Human Growth Hormone (hGH) by a Novel Form of a Modified Recombinant hGH" *Endocrinology* 118:720 (1986).

Gohda et al., "Purification and Partial Characterization of Hepatocyte Growth Factor from Plasma of a Patient with Fulminant Hepatic Failure" *J. Clin. Invest.* 81:414–419 (1988).

Hanks et al., "The Protein Kinase Family: Conserved Features and Deduced Phylogeny of the Catalytic Domains" *Science* 241:42–52 (1988).

Heidaran et al., "Role of alpha beta receptor heterodimer formation in beta platelet–derived growth factor (PDGF) receptor activation by PDGF–AB" *Journal of Biological Chemistry* 266:20232–20237 (1991).

Hernandez et al., "Characterization of the Effects of Human Placental HGF on Rat Hepatocytes" *J. Cell Phys.* 150(1):116–121 (1992).

Hoogenboom et al., "Construction and Expression of Antiobody–Tumor Necrosis Factor Fusion Proteins" *Molecular Immunology* 28:1027–1037 (1991).

Lokker et al., "Generation and Characterization of a Competitive Antagonist of Human Hepatocyte Growth Factor, HGF/NK1" *Journal of Biological Chemistry* 268(23):17145–17150 (Aug. 15, 1993).

Mascarelli et al., "Heterocomplex formation betweeen high and low affinity FGF receptors is mediated by the formation of a FGF dimer" *Bulletin du Cancer* 80(9):786–798 (1993).

Miyazawa et al., "An Alternatively Processed mRNA Generated from Human Hepatocyte Growth Factor Gene" *European Journal of Biochemistry* 197:15–22 (1991).

Miyazawa et al., "Molecular Cloning and Sequence Analysis of cDNA for Human Hepatocyte Growth Factor" *Biochem.*

(List continued on next page.)

*Primary Examiner*—Paula K. Hutzell
*Assistant Examiner*—Robert C. Hayes
*Attorney, Agent, or Firm*—Diane L. Marschang; Deirdre L. Conley

[57] ABSTRACT

The invention concerns a method for activating receptors selected from receptor tyrosine kinases, cytokine receptors and members of the nerve growth factor receptor superfamily. A conjugate comprising the direct fusion of at least two ligands capable of binding to the receptor(s) to be activated is contacted with the receptors, whereby the ligands bind their respective receptors inducing receptor oligomerization.

4 Claims, 9 Drawing Sheets

OTHER PUBLICATIONS

& Biophys. Res. Comm. 163(2):967–973 (Sep. 15, 1989).

Munro, "Uses of chimaeric antibodies" *Nature* 312:597 (1984).

Nakamura et al., "Molecular Cloning and Expression of Human Hepatocyte Growth Factor" *Nature* 342:440–443 (Nov. 23, 1989).

Nakamura et al., "Purification and Characterization of a Growth Factor from Rat Platelets for Mature Parenchymal Hepatocytes in Primary Cultures" *Proc. Natl. Acad. Sci, USA* 83:6489–6493 (1986).

Nakamura et al., "Purification and Subunit Structure of Hepatocyte Growth Factor from Rat Platelets" *FEBS Letters* 224(2):311–316 (Nov. 1987).

Ogura et al., "Molecular Mechanism for the Formation of the High–Affinity Complex of Interleukin 2 and its Receptor" *Mol. Biol. Med.* 5:123–138 (1988).

Okajima et al., "Primary Structure of Rat Hepatocyte Growth Factor and Induction of Its mRNA During Liver Regeneration Following Hepatic Injury" *European Journal of Biochemistry* 193:375–381 (1990).

Pandit et al., "Three–dimensional structure of dimeric human recombinant macrophage colony–stimulating factor" *Science* 258:1358–1362 (1992).

Rubin et al., "A Broad–Spectrum Human Lung Fibroblast–Derived Mitogen is a Variant of Hepatocyte Growth Factor" *Proc. Natl. Acad Sci, USA* 88:415–419 (1991).

Seki et al., "Isolation and Expression of cDNA for Different Forms of Hepatocyte Growth Factor from Human Leukocyte" *Biochem. and Biophys. Res. Commun.* 172(1):321–327 (Oct. 15, 1990).

Tashiro et al., "Deduced Primary Structure of Rat Hepatocyte Growth Factor and Expression of the mRNA in Rat Tissues" *Proc. Natl. Acad. Sci. USA* 87:3200–3204 (1990).

Ullrich and Schlessinger, "Signal Transduction by Receptors with Tyrosine Kinase Activity" *Cell* 61:203–212 (Apr. 1990).

Yarden et al., "Growth Factor Receptor Tyrosine Kinases" *Ann. Rev. Biochem.* 57:443–478 (1988).

Chan et al. Science 254 (1991) 1382–1385.

Matsumoto et al. Biochem and Biophys. Res. Comm. 181(1991) 691–699.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

TTGGAATCCC ATTACAACC TCGAGTTGTT TCGTTTTGGC ACAAGAT 4 7

( 2 ) INFORMATION FOR SEQ ID NO:2:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

GAATCCCATT TACGACGTCC AATTGTTTCG    30

( 2 ) INFORMATION FOR SEQ ID NO:3:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

CCCATTTACA ACTGCCAATT GTTTCG    26

( 2 ) INFORMATION FOR SEQ ID NO:4:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

AGAAGGGAAA CAGTGTCGTG CA    22

( 2 ) INFORMATION FOR SEQ ID NO:5:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

AGTGGGCCAC CAGAATCCCC CT    22

( 2 ) INFORMATION FOR SEQ ID NO:6:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

TCCACGACCA GGAGAAATGA CAC    23

( 2 ) INFORMATION FOR SEQ ID NO:7:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

GCATTCAACT TCTGAGTTTC TAATGTAGTC    30

( 2 ) INFORMATION FOR SEQ ID NO:8:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

CATAGTATTG TCAGCTTCAA CTTCTGAACA    30

( 2 ) INFORMATION FOR SEQ ID NO:9:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

TCCATGTGAC ATATCTTCAG TTGTTTCCAA　　　　　　　　　　　　　　　　30

( 2 ) INFORMATION FOR SEQ ID NO:10:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

TGTGGTATCA CCTTCATCTT GTCCATGTGA　　　　　　　　　　　　　　　　30

( 2 ) INFORMATION FOR SEQ ID NO:11:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO:11:

ACCTTGGATG CATTAAGTTG TTTC　　　　　　　　　　　　　　　　　　　24

( 2 ) INFORMATION FOR SEQ ID NO:12:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:12:

TTGTCCATGT GATTAATCAC AGT　　　　　　　　　　　　　　　　　　　　23

( 2 ) INFORMATION FOR SEQ ID NO:13:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( x i ) SEQUENCE DESCRIPTION: SEQ ID NO:13:

GTTCGTGTTG GGATCCCATT TACCTATCGC AATTG　　　　　　　　　　　　35

( 2 ) INFORMATION FOR SEQ ID NO:14:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:14:

AGCTTGCCTC GAGGCA　　　　　　　　　　　　　　　　　　　　　　　　16

( 2 ) INFORMATION FOR SEQ ID NO:15:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ATGAAGCCC  CCGCTGTGCT  TGCACCTGGC  ATCCTCGTGC  TCCTGTTTAC                50

C                                                                        51
```

( 2 ) INFORMATION FOR SEQ ID NO:16:

( i ) SEQUENCE CHARACTERISTICS:
        ( A ) LENGTH: 60 bases
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
CACTAGTTAG  GATGGGGGAC  ATGTCTGTCA  GAGGATACTG  CACTTGTCGG               50

CATGAACCGT                                                               60
```

( 2 ) INFORMATION FOR SEQ ID NO:17:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
TAGTACTAGC  ACTATGATGT  CT                                               22
```

( 2 ) INFORMATION FOR SEQ ID NO:18:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
TTTACTTCTT  GACGGTCCAA  AG                                               22
```

( 2 ) INFORMATION FOR SEQ ID NO:19:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
CAGGGGGAGT  TGCAGATTCA  GCTGT                                            25
```

( 2 ) INFORMATION FOR SEQ ID NO:20:

( i ) SEQUENCE CHARACTERISTICS:
        ( A ) LENGTH: 45 bases
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
AGTTTTGTCG  GTGACCTGAT  CATTCTGATC  TGGTTGAACT  ATTAC                    45
```

( 2 ) INFORMATION FOR SEQ ID NO:21:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: linear ( x i ) SEQUENCE DESCRIPTION: SEQ ID NO:21:

CACAGTCG         8

( 2 ) INFORMATION FOR SEQ ID NO:22:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:22:

GTGACCGACT GTGGTAC         17

( 2 ) INFORMATION FOR SEQ ID NO:23:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( x i ) SEQUENCE DESCRIPTION: SEQ ID NO:23:

ACTGTGCAAT TAAAACATGC GAGACG         26

( 2 ) INFORMATION FOR SEQ ID NO:24:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( x i ) SEQUENCE DESCRIPTION: SEQ ID NO:24:

GTGACCGTCT CGCATGTTTT AATTGCACAG T         31

( 2 ) INFORMATION FOR SEQ ID NO:25:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:25:

GTCGGTGACC GTCTCTTCAA CTTCTGAACA         30

RECEPTOR ACTIVATION WITH INACTIVE HEPATOCYTE GROWTH FACTOR LIGANDS

This is a continuation of application Ser. No. 08/423,291 filed on 17 Apr., 1995, now abandoned, which is a divisional of Ser. No. 08/268,880 filed 30 Jun., 1994, now abandoned, which is a continuation application of Ser. No. 07/950,572 filed 20 Sep., 1992, now abandoned, which is a continuation-in-part application of Ser. No. 07/884,811 filed 18 May, 1992 (issued as U.S. Pat. No. 5,316,921) and a continuation-in-part application of Ser. No. 07/885,971 filed 18 May, 1992 (issued as U.S. Pat. No. 5,328,837 which applications are incorporated herein by reference and to which application(s) priority is claimed under 35 USC § 120.

FIELD OF THE INVENTION

This application relates to a method for receptor activation. More particularly, the invention concerns a method for ligand-induced oligomerization of cell-surface receptors. The invention further relates to methods for making ligand variants that act as competitive agonists of the respective native ligands, and to ligand-immunoglobulin chimeras.

BACKGROUND OF THE INVENTION

Many polypeptides, such as growth factors, differentiation factors, and hormones mediate their actions by binding to and activating cell surface receptors. Although the mechanism of receptor activation varies for specific receptor-ligand pairs and is often not entirely understood, it is a common feature of many receptors that they need to be oligomerized to become active, or that their activity is enhanced by oligomerization. Growth factor receptors with tyrosine kinase activity (receptor tyrosine kinases) and certain cytokine receptors are typical representatives of such receptors.

Receptors with tyrosine kinase activity have a similar molecular topology. They all possess an extracellular ligand binding domain, a hydrophobic transmembrane domain, and a cytoplasmic domain that contains a tyrosine kinase catalytic domain, and can be further classified on the basis of sequence similarity and distinct structural characteristics [Hanks, S. K. et al., *Science* 241, 42–52 (1988); Yarden, Y. and Ullrich, A., *Annu. Rev. Biochem.* 57, 443–478 (1988)]. Monomeric subclass I receptors have two cysteine-rich repeat sequences in the extracellular domain; subclass II receptors have disulfide-linked heterotetrameric $\alpha_2\beta_2$-type structures with similar cysteine-rich repeat sequences; whereas the extracellular domains of subclass III and IV receptors have five or three immunoglobulin-like repeats, respectively. For example, receptors for insulin, epidermal growth factor (EGF), platelet-derived growth factor (PDGF), insulin-like growth factor (IGF-1), colony-stimulating factor 1 (CSF-1), and hepatocyte growth factor (HGF) belong in this family.

Because of their configuration, receptor tyrosine kinases can be envisioned as membrane-associated allosteric enzymes. As in these receptors, in contrast to water-soluble enzymes, the ligand binding domain and the tyrosine kinase catalytic domain (protein tyrosine kinase activity) are separated by the plasma membrane, receptor activation due to extracellular ligand binding must be translated across the membrane barrier in order to activate intracellular domain functions.

According to an allosteric receptor oligomerization model, ligand binding and the resultant conformational alteration of the extracellular domain induce receptor oligomerization, which, in turn, stabilizes interactions between adjacent cytoplasmic domains and leads to activation of kinase function by molecular interaction. Receptor oligomerization permits the transmission of a conformational change from the extracellular domain to the cytoplasmic domain without requiring alterations in the positioning of amino acid residues within the transmembrane domain. The monomeric inactive receptors are in equilibrium with oligomeric activated receptors. The binding of growth factors to their receptors stabilizes an oligomeric state which possesses enhanced ligand-binding affinity and elevated protein tyrosine kinase activity [Schlessinger, J.,*J. Cell Biol.* 103, 2067–2072 (1986); Yarden, Y. and Schlessinger, J., *Biochemistry* 26, 1434–1442 (1987); Yarden, Y. and Schlessinger, J., *Biochemistry* 26, 1443–1451 (1987)]. A more general allosteric receptor oligomerization model is described in Schlessinger, J., *Trends Biochem. Sci.* 13, 443–447 (1988).

Receptor oligomerization which, for sake of simplicity, is commonly illustrated by receptor dimerization, may be induced by monomeric ligands, such as EGF, that induce conformational changes resulting in receptor-receptor interactions [Cochet, C. et al., *J. Biol. Chem.* 263, 3290–3295 (1988)]. Bivalent ligands, such as PDGF and CSF-1 mediate dimerization of neighboring receptors [Heldin, C. H. et al., *J. Biol. Chem.* 264, 8905–8912 (1989); Hammacher, A. et al., *EMBO J.* 8, 2489–2495 (1989)].

The universality of this receptor activation model for all receptor tyrosine kinases is supported by reports about the construction of fully functional chimeric receptors consisting of major domains of different tyrosine kinase receptor subclasses [Riedel, H. et al., *EMBO J.* 8, 2943–2954 (1989) ]. Although in some cases heterodimer formation between structurally very similar receptors [Hammacher, A. et al., supra for α- and β-type PDGF receptors; Soos, M. A. and Siddle, K., *Biochem. J.* 263, 553–563 (1989) for insulin and IGF-1 receptors] has also been demonstrated, direct proof that such hybrid receptors are indeed functional is not yet available. In general, more detailed analyses of the structural perturbations and requirements for ligand-induced alterations in receptor tyrosine kinases has been hampered by the complexities of these membrane associated systems and by the lack of suitable quantities of highly purified natural or recombinant receptors.

For a general review of the signal transduction by receptors with tyrosine kinase activity see Ullrich, A. and Schlessinger, J., *Cell* 81, 203–212 (1990), and Bormann, B. J. and Engelman, D. M.,*Annu. Rev. Biophys. Biomol. Struct.* 21, 223–266 (1992), and the references cited therein.

A more recently discovered receptor tyrosine kinase is the HGF receptor (HGFr), which has been identified as the product of the c-MET proto-oncogene [Bottaro et al., *Science* 251, 802–804 (1991); Naldini et al ., *Oncogene* 6, 501–504 (1991)]. MET was originally identified as a transforming gene in a chemically treated osteogenic sarcoma cell line that had undergone a chromosomal translocation [Park, M. et al., *Cell* 45, 895–904 (1986)]. The mature HGFr is a disulfide linked heterodimer which arises by proteolytic processing of a glycosylated 190-kDa precursor into a 50-kDa α-subunit and a 145-kDa β-subunit [Giordano, S. et al., *Oncogene* 4, 1383–1388 (1989)]. The α-subunit is extracellular and the β-subunit contains an extracellular region, a single membrane-spanning domain and a tyrosine kinase domain. On normal cells, binding of HGF is required to activate the tyrosine kinase activity of HGFr. The HGFr protein becomes phosphorylated on tyrosine residues of the 145-kDa β-subunit upon HGF binding.

Receptor oligomerization (dimerization) also appears to be critical for signaling by certain cytokine receptors, particularly in a recently discovered superfamily of single transmembrane receptors, designated as the hematopoietin receptor superfamily [Bazan, et al., *Biochem. Biophys. Res. Commun.* 164, 788–795 (1989); D'Andrea, A. D., et al., *Cell* 58, 1023–1024 (1989); Gearing, D. P. et al., *EMBO J.* 8, 3667–3676 (1989); Itoh, N. et al., *Science* 247, 324–327 (190); Idzerda, R. L. et al., *J. Exp. Med.* 171, 861–873 (1990); Godwin, R. G. et al., *Cell* 60, 941–951 (1990); Fukunaga, R. et al., *Cell* 61, 341–350 (1990); Bazan, J. F. et al., *Proc. Natl. Acad. Sci. USA* 87, 6934–6938 (1990); Patthy, L., *Cell* 61, 13–14 (1990); Abdel-Meguid, S. S. et al., *Proc. Natl. Acad. Sci. USA* 84, 6434–6437 (1987); De Vos et al., *Science* 255, 306–312 (1992); Cosman, D. et al., *Trends Biochem. Sci.* 15, 265–270 (1990)]. The members of this superfamily include the receptors for growth hormone (GH), prolactin (PRL), placental lactogen (PL), and other cytokine and hematopoietic receptors, such as the receptors for interleukins 1 to 7 (IL-1, IL-2, the β-subunit also known as p75, IL-3, IL-4, IL-5, IL-6, IL-7), erythropoietin (EPO), granolocyte colony stimulating factor (G-CSF), macrophage colony stimulating factor (M-CSF) and granulocyte-macrophage colony stimulating factor (GM-CSF). These receptors contain homologous extracellular ligand-binding domains and highly variable intracellular domains that are not homologous to any known tyrosine kinase or other protein.

Recently Cunningham, B. C. et al., *Science* 254, 821–825 (1991) published evidence that dimerization is important for activation of hGH and other cytokine receptors. To analyze the structural requirements and mechanism for hormone-induced changes in hGH, the authors used the extracellular domain of the hGH receptor (hGH binding protein, hGHbp) produced in high yield by expression in *E. coli*. Results of crystallization, size exclusion chromatography, calorimetry studies and a fluorescence quenching assay showed that hGH forms a 1:2 complex with the extracellular domain of hGHbp. Based upon these and further studies it was concluded that hGH contains two functionally distinct sites for binding to two overlapping sites on the hGHbp in producing the hGH. (hGHbp)$_2$ complex, and that the formation of an analogous dimeric receptor complex on the cell surface is critical to the signal transduction mechanism of hGH and probably homologous cytokine receptors. The receptor dimerization mechanism was confirmed by the finding that a hGH analog lacking the second receptor binding site (and therefore unable to dimerize hGHbp) had decreased receptor binding affinity and decreased receptor down regulation to saturation.

Yet another example is the superfamily of nerve growth factor receptor (NGFR) related receptors, such as the tumor necrosis factor (TNF) receptors TNFR-I and TNFR-II, the Fas and Aps gene products, and several T and B cell surface antigens. Currently included in this superfamily are NGFR, found on neural cells, the B-cell antigen CD40, the MRC OX-40 antigen, which is a marker of activated T cells of the CD4 phenotype, TNFR-I and TNFR-II which are found on a variety of cell types, a cDNA (4-1BB) which encodes a protein of unknown function and is obtained from T-cell clones, and SFV-T2, an open reading frame in Shope fibroma virus. The members of this family are characterized by three or four cysteine-rich motifs of about 40 amino acids in the extracellular domain of the molecule, and in some cases by a hinge-like region but no other domain types. Functionally, those members of this receptor superfamily that have so far been characterized are usual in that they are able to react with more than one ligand, and that these ligands are polymeric in nature. It has been shown that the TNF receptors are activated by oligomerization because bivalent anti-TNFR antibodies but not monovalent antibody fragments (Fab' fragments) were found to activate TNFR [Engelman, H. et al., *J. Biol. Chem.* 265, 14497–14504 (1990), and the references cited therein]. It was suggested that a TNF-α trimer may trigger signal transduction by cross-linking two cell surface TNFR molecules [Ashkenazi, A. et al., *Proc. Natl. Acad. Sci. USA* 88 10535–10539 (1991)]. Similarly, the Fas and Aps gene products can be activated by antibodies.

An object of the present invention is to provide methods for ligand-induced receptor oligomerization.

It is another object to provide methods for making ligand variants that act as competitive agonists of the corresponding native ligands.

It is a further object to provide methods for substantially recovering ligand biological activity lost as a result of a mutation.

It is a still further object to provide methods for converting ligands that are competitive antagonist of the action of their native counterparts into agonists.

It is yet another object to increase the half-life of ligands.

SUMMARY OF THE INVENTION

The present invention is based on observations obtained with a series of recombinant huHGF (rhuHGF) variants. The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the hHGF cDNA reveals that both the α- and the β-chains are contained in a single open reading frame coding for a pre-pro precursor protein. In the predicted primary structure of mature hHGF, an interchain S—S bridge is formed between Cys 487 of the α-chain and Cys 604 in the β-chain. The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four Kringle domains. The Kringle 1 domain extends from about aa 128 to about aa 206, the Kringle 2 domain is between about aa 211 and about aa 288, the Kringle 3 domain is defined as extending from about aa 303 to about aa 383, and the Kringle 4 domain extends from about aa 391 to about aa 464 of the α-chain.

rhuHGF variants were produced to determine the structural and functional importance of the cleavage of the prohormone to the α/β dimer and of the kringle and protease-like domains. A series of C-terminal truncations of huHGF were made by deleting either the β-chain or the β-chain in addition to a progressive number of kringle domains, and mutations were introduced at the one-chain to two-chain cleavage site, or within the protease domain.

Some of the huHGF variants retained the ability to bind to their receptor (HGFr) with high affinity, but were defective in HGF biological (mitogenic) activity, and exhibited a reduced ability to induce phosphorylation of the HGFr.

It has been found that conformationally correct chimeric proteins comprising the fusion of such variant HGF molecules to an immunoglobulin constant domain sequence can be made, and that such chimeras retain the ability to bind the HGFr.

In has further been found that the biological activity of HGF variants that were formerly capable of binding their receptor but lacked or exhibited substantially reduced HGF biological activity as compared to wild-type huHGF could be substantially recovered in the form of HGF variant-immunoglobulin chimeras.

Although the mechanism by which binding of HGF to HGFr activates the intracellular tyrosine kinase is not fully understood, it is believed that receptor activation by the HGF variant-immunoglobulin chimeras tested is due to the structural ability of the HGF-immunoglobulin heavy chain dimers to induce receptor dimerization. HGF ligands coupled (oligomerized) by any other methods, e.g. via cysteine bridges, may induce receptor activation in an analogous manner.

Other receptors that require oligomerization for (full) biological activity can also be activated by oligomerized (e.g. dimerized) ligand sequences, such as by chimeric molecules comprising receptor binding domain(s) from the corresponding native or variant ligands fused to an immunoglobulin constant domain sequence. Such receptors include other receptors with tyrosine kinase activity, such as receptors for insulin, EGF, PDGF, IGF-1, CSF-1; cytokines, e.g. members of the hematopoietin receptor superfamily, such as hGH, hPRL, IL-1, IL-2, IL-3, IL-4, IL-5, IL-6, IL-7, erythropoietin, G-CSF, M-CSF, and GM-CSF; and members of the NGFR superfamily, such as NGFR, TNFR-I, TNFR-II.

In one aspect, the present invention concerns a method for receptor activation comprising (a) providing a conjugate comprising the direct fusion of a first ligand and a second ligand capable of binding to first and second receptors, respectively, wherein the first and second receptors are capable of oligomerization with each other, and are selected from the group consisting of receptors with tyrosine kinase activity, cytokine receptors, and members of the nerve growth factor receptor superfamily, and (b) contacting the conjugate with the first and second receptors whereby the first ligand binds to the first receptor and the second ligand binds to the second receptor.

In another aspect, the invention concerns a method for receptor activation comprising (a) providing a conjugate comprising a first ligand and a second ligand capable of binding to first and second receptors, respectively, wherein the first and second receptors are selected from receptors with tyrosine kinase activity, and (b) contacting the conjugate with the first and second receptors whereby the first ligand binds to the first receptor and the second ligand binds to the second receptor. In this embodiment, the first and second ligands may be directly fused to each other or may be connected by a covalent linkage comprising a heterologous linker. The heterologous linker may, for example comprise an immunoglobulin constant and/or variable domain sequence, a moiety from a nonproteinaceous cross-linking agent, a disulfide bridge between the first and second ligands, or a polypeptide spacer sequence.

In a further aspect, the invention relates to a method for recovering the biological activity of a ligand variant capable of selective binding to a receptor selected from the group consisting of receptors with tyrosine kinase activity, cytokine receptors, and members of the nerve growth factor receptor superfamily, comprising:

a) directly fusing two molecules of the ligand variant to obtain a homodimer; or b) fusing the ligand variant to a second receptor binding amino acid sequence to obtain a heterodimer; and c) contacting the homo- or heterodimer with the receptor such that one molecule of the ligand variant binds to a first molecule of the receptor and a second molecule of the ligand variant or the second receptor binding sequence binds to a second molecule of the receptor.

If the receptor is from the family of receptor tyrosine kinases, the two ligand variants may be directly fused to each other, or, alternatively, may be connected by a heterologous linker.

In a still further aspect, the invention concerns a method for making an agonist for a native ligand of a receptor with tyrosine kinase activity, comprising dimerizing a first ligand variant capable of binding to the receptor or coupling the first variant with a second ligand variant capable of binding to the receptor.

In yet another aspect, the invention concerns a chimeric molecule comprising a fusion of a first ligand capable of binding to a receptor with tyrosine kinase activity to a first immunoglobulin constant domain sequence, and a fusion of a second ligand capable of binding to said receptor or to another receptor with tyrosine kinase activity to a second immunoglobulin constant domain sequence.

DETAILED DESCRIPTION OF THE INVENTION

Figure 1:
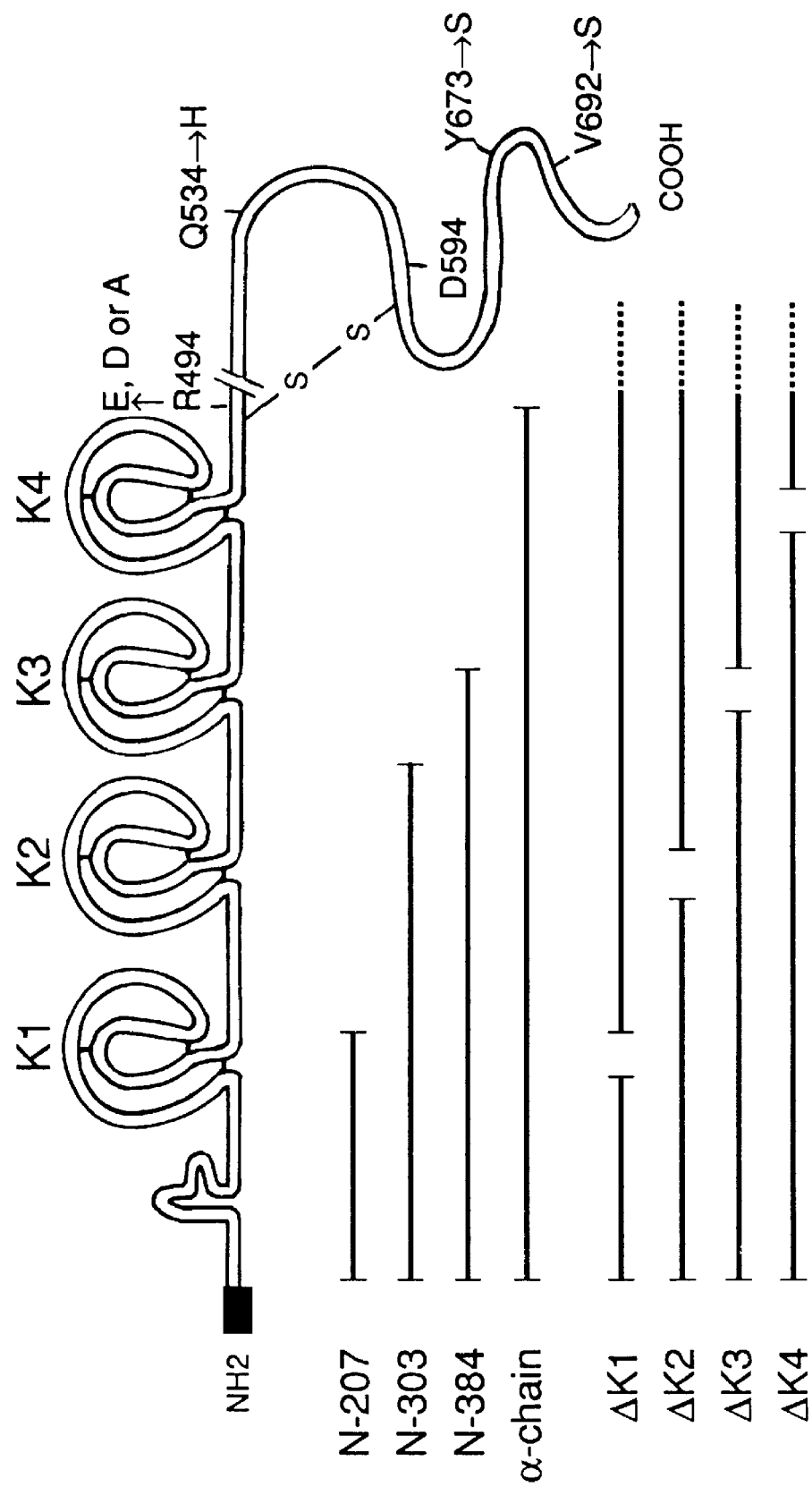
FIG. 1 is a schematic representation of the α- and β-subunits of huHGF. Shown in the α-chain are the signal sequence (boxed region) which encompasses amino acids 1–31, the predicted finger and four Kringle domains, each with their respective three disulfide bonds. The cleavage site for generation of the heterodimeric α/β form of huHGF immediately follows the P1 cleavage residue R494. This last residue has been specifically substituted with either E, D or A to generate HGF single-chain variants. The β-chain, which follows the cleavage site, contains homology to serine proteases. It is proposed that the α- and β-chains are held together by a unique disulfide-bridge between C487(α) and C604(β) (Nakamura et al., 1989, supra). Three residues within the β-chain have been substituted individually or in combination to reconstitute the authentic residues of a serine-protease. Schematic representations of the mature forms of the C-terminal truncation variants are depicted below: N-207, deleted after the first Kringle; N-303, deleted after the second Kringle; N-384, deleted after the third Kringle and the α-chain. Also shown are the variants where deletions of each of the Kringles (ΔK1, ΔK2, ΔK3 and ΔK4) were introduced. In each case, the deletions specifically remove the entire Kringle from C1 to C6.

For the purpose of the present invention the "receptor" can be any cell-surface receptor selected from receptors with tyrosine kinase activity, cytokine receptors and members of the nerve growth factor receptor superfamily, the activation or signaling potential of which is mediated by oligomerization, irrespective of the actual mechanism by which the receptor oligomerization is induced, wherein "oligomerization" specifically includes dimerization as well as the formation of higher oligomers. The definition includes cell-surface receptors that are normally activated a) by monomeric ligands (ligands with one receptor binding domain), such as EGF, that induce conformational changes in the extracellular domain resulting in receptor-receptor interactions, b) by bivalent ligands (ligands with two receptor binding domains), such as PDGF, CSF-1, and hGH that mediate dimerization of neighboring receptors, or c) by interaction of the ligand with a disulfide stabilized receptor dimer and subsequent intracomplex conformational change, such as insulin or IGF-1. Specifically covered by this definition are receptors with tyrosine kinase activity (receptor tyrosine kinases) and members of the hematopoietin and nerve growth factor receptor superfamilies.

"Cytokine" is a generic term for proteins released by one cell population which act on another cell as intercellular mediators. Included among the cytokines are growth hormone, insulin-like growth factors, interleukins, hGH, N-methionyl hGH, bovine growth hormone, parathyroid hormone, thyroxine, insulin, proinsulin, relaxin, prorelaxin, glycoprotein hormones such as, follicle stimulating hormone (FSH), thyroid stimulating hormone (TSH), and leutinizing hormone (LH), hemopoietic growth factor, HGF, fibroblast growth factor, prolactin, placental lactogen, tumor necrosis factor-α and -β (TNF-α and -β), muellerian inhibiting substance, mouse gonadotropin-associated peptide, inhibin, activin, vascular endothelial growth factor, integrin, thrombopoietin, nerve growth factors, such as NGF-β, PDGF, transforming growth factors (TGFs) such as, TGF-α and TGF-β, insulin-like growth factor-1 and -2 (IGF-1 and IGF-2), erythropoietin, osteoinductive factors, interferons (IFNs) such as, IFN-α, IFN-β and IFN-γ, colony stimulating factors (CSFs) such as, M-CSF, GM-CSF, and G-CSF, interleukins (ILs) such as, IL-1, IL-2, IL-3, IL-4, IL-5, IL-6, IL-7, IL-8 and other polypeptide factors. Cytokine receptors are receptors binding to cytokines as hereinabove defined.

The expressions "receptor with (protein) tyrosine kinase activity" and "receptor tyrosine kinase" and grammatical variants thereof, are used interchangeably and refer to receptors typically having a large extracellular ligand binding domain, a single hydrophobic transmembrane region and a tyrosine kinase catalytic domain, which can be classified into subclasses (subclasses I–IV according to present knowledge) based upon their sequence similarity and distinct structural characteristics as defined by Schlessinger, J. (1988) Supra, and Ullrich, A. and Schlessinger, J. (1990), Supra. Among other highly conserved sequences of unknown function, the tyrosine kinase domain of these receptors contains a consensus sequence Gly-X-Gly-X-X-Gly-X(15–20)Lys that functions as part of the binding site for ATP. Receptor tyrosine kinases catalyze the phosphorylation of exogenous substrates as well as tyrosine residues within their own polypeptide chains. This family includes the insulin receptor (insulin-R), epidermal growth factor receptor (EGF-R), platelet-derived growth factor receptors A and B (PDGF-R-A and -B), insulin-like growth factor receptor (IGF-1-R), cology-stimulating factor 1 receptor (CSF-1-R), hepatocyte growth factor receptor (HGFr), HER2/neu, HER3/c-erbB-3, IRR, Xmrk and receptors for acidic fibroblast growth factor (FGF) and basic FGF, termed flg and bek. The oligomerization mechanism implies the possible existence of hybrid complexes between structurally very similar receptors such as PGDF-R-A and -B, EGF-R and HER2/neu, or insulin-R and IGF-1-R [Hammacher et al. (1989), supra; Soos, M. A. and Siddle, K., Biochem. J. 263, 553–563 (1989)].

EGF-R can serve as a model for subclass I receptor tyrosine kinases activated by a monovalent ligand. EGF-R is a single-chain polypeptide of about 170,000 kD composed of a large extracellular ligand binding domain, a single hydrophobic membrane spanning region, and a cytoplasmic region with intrinsic protein tyrosine kinase activity [Ullrich, A. et al., Nature 309, 418–425 (1984)]. Yarden and Schlessinger [Biochemistry 26, 1434–1442 (1987); Biochemistry 24, 1443–1451 (1987)] demonstrated that purified EGF-R undergoes rapid, reversible EGF-induced oligomerization and that receptor oligomerization is an intrinsic property of the EGF-R. Similar results were obtained in living cells by Cochet, C. et al. [J. Biol. Chem. 263, 3290–3295 (1988)]. Based upon earlier structure-function studies and initial data from electron microscopic characterization of the purified extracellular domain of the EGF receptor, a four-domain model for the organization of the extracellular portion of the EGF receptor was proposed by Ullrich, A. and Schlessinger, J. (1990), supra. In this model, "domain III" and "domain I" are proposed to contribute most of the determinants that enable the receptor to interact specifically with its ligand (EGF or transforming growth factor-α -TGF-α), and it is suggested that the EGF-binding region lies in the cleft formed between domains III and I. HER2/neu [Lee, J. et al., *EMBO J.* 8, 167–173 (1989); Hazan, R. et al., *Cell. Growth Differ.* 1, 3–7 (1990)], HER3/c-erbB-3 [Kraus, M. H. et al., *Proc. Natl. Acad. Sci. USA* 86, 9193–9197 (1989)] and Xmrk [Wittbrodt, J. et al., *Nature* 341, 415–421 (1989)] belong in this subclass.

Typical representatives of the subclass II receptor tyrosine kinases are the insulin-R and IGF-1-R [Ullrich et al., *Nature* 313, 756–761 (1985); Ullrich et al., *EMBO J.* 5, 2503–2512 (1986); Ebina, Y. et al., *Cell* 40, 747–758 (1985); Perdue, J. F., Can. J. *Biochem. Cell. Biol.* 62, 1237–1245 (1984); Rechler, M. M. and Nissley, S. P., *Ann. Rev. Physiol.* 47, 425–442 (1985), and the references cited in these review articles; Lee et al., *Mol. Endocrinol.* 2, 404–422 (1988); Wilson et al., *Mol. Endocrinol.* 2, 1176–1185 (1988); Morgan et al., *Nature* 329, 3071–3072 (1987)]. Ligand binding to these receptors, which have a heterotetrameric structure [Lammer, R. et al., *EMBO J.* 8, 1369–1375 (1989); Czech, M. *Cell* 59, 235–238 (1989)], induces allosteric interaction of two αβ halves within the disulfide bridge stabilized receptor complex [Ullrich, A. (1990), supra]. This subclass also includes IRR, a putative receptor for a ligand of the insulin family [Shier, P. and Watt, V. M., *J. Biol. Chem.* 264, 14605–14608 (1989)].

Subclass III receptor tyrosine kinases bind dimeric ligands that mediate dimerization of neighboring receptors. This subclass is represented by receptors for PDGF-A and -B, and CSF-1. Human PGDF occurs as three isoforms which are made up of disulfide-bonded A and B chains. The isoforms bind to two different but structurally related cell surface receptors: PGDF-R-A and PGDF-R-B. The A-type receptor binds all three isoforms (PGDF-AA, PGDF-AB, and PGDF-BB), whereas the B-type receptor only binds PGDF-BB and PGDF-AB. It has been suggested that PDGF is a bivalent ligand that activates its receptor by dimerization [Hammacher, A. et al., *EMBO J.* 8, 2489–2495 (1989)], and shown that dimerization occurs after ligand binding and is closely associated with receptor kinase activation [Heldin, C-H et al., *J. Biol. Chem.* 264, 8905–8912 (1989)].

Subclass IV of the tyrosine kinase receptors includes the recently described receptors for acidic FGF (FGF-R flg) and basic FGF (FGF-R bek) [Ruta, M. et al., *Proc. Natl. Acad. Sci. USA* 86, 8722–8726 (1989) and Pasquale, E. B. and Singer, S. J., *Proc. Natl. Acad. Sci. USA* 86, 5449–5453 (1989), and references cited therein]. These receptors exhibit three related sequence repeats in their extracellular domains, and show weak but significant homology with the corresponding region of IL-1 receptor.

The expression "hematopoietin receptor superfamily" is used to define single-pass transmembrane receptors, with a three-domain architecture: an extracellular domain hat binds the activating ligand, a short transmembrane segment, and a domain residing in the cytoplasm. The extracellular domains of these receptors have low but significant homology within their extracellular ligand-binding domain comprising about 200–210 amino acids. The homologous region is characterized by four cysteine residues located in the N-terminal half of the region, and a Trp-Ser-X-Trp-Ser (WSXWS) motif located just outside the membrane-spanning domain. Further structural and functional details of these receptors are provided by Cosman, D. et al., (1990), supra. The receptors of IL-1, IL-2, IL-3, IL-4, IL-5, IL-6, IL-7, prolactin, placental lactogen, growth hormone GM-CSF, G-CSF, M-CSF and erythropoietin have, for example, been identified as members of this receptor family.

IL-2-induced oligomerization of the IL-2 receptor was reported, for example, by Ogura, T. et al., *Mol. Biol. Med.* 5, 123–13 (1988). They have shown that high-affinity binding of IL-2 to its receptor gives rise to the formation of a ternary complex, comprising the IL-2 receptor α-subunit (p55), the β-subunit (p75, also referred to as the "converter"), and IL-2, by chemical crosslinking. The dimerization of the extracellular domain of hGH-R by a single hGH molecule was proposed to be relevant to the signal transduction mechanism for hGH receptor and other related cytokine receptors by Cunningham, B. C. et al., (1991), supra.

The expression "nerve growth factor receptor (NGFR) superfamily" is used to describe a family of membrane proteins defined by the presence of cysteine-rich motifs originally identified in the low-affinity NGFR. This superfamily, which was first described by Mallett, S. and Barclay, A. N., supra, includes two receptors for tumor necrosis factor (TNFR-I and TNFR-II) and two lymphocyte proteins of so far undetermined function.

The terms "first receptor" and "second receptor" as used throughout the specification and the claims are used to designate receptors that are capable of heterooligomer (heterodimer) formation in vivo as a result of ligand-induced receptor activation. Such receptors are usually located on similar (preferably identical) cell types, and may, but do not need to, exhibit structural homology. In a specific embodiment, the first and the second receptors exhibit at least about 75% homology, and preferably at least about 80%, more preferably at least about 85% homology in their active domains, and preferably have similar physiological functions. It has been mentioned before that hetero-receptor complexes might exist between receptors such as PGDF-R-A and -B, EGF-R and HER2/neu, or insulin-R and IGF-1-R. Receptors for HGF and an HGF-like protein encoded by a gene recently identified on the DNF15S2 locus on human chromosome 3 (3p21) [Han, S. et al., *Biochemistry* 30, 9768–9780 (1991)] are also candidates for heterodimer formation. Heterodimer formation between two receptors can be detected by standard methods of analytical chemistry, e.g. nondenaturing gel electrophoresis. In a preferred method, the interaction of the receptors can be stabilized by utilizing a covalent cross-linking agent, essentially as described for EGF-R by Cochet, C. et al. (1988), supra, and the covalently linked, cross-linked receptors can be analyzed by SDS gel-electrophoresis.

The term "ligand" is used to designate an organic molecule, or a peptide or polypeptide sequence capable of specific binding to a receptor as hereinabove defined. The definition includes any native ligand for a receptor or any region or derivative thereof retaining at least a qualitative receptor binding ability. Specifically excluded from this definition are (agonist and antagonist) antibodies to a receptor.

In the molecules used in accordance with the present invention, the first and second ligands may be identical or different, and include two different receptor binding domains from a native bivalent ligand, or at least the receptor binding domains from two identical or different ligands for the same or two different receptors, and derivatives of such native receptor binding sequences. It has been proposed that hybrid complexes might exist between structurally and/or functionally similar receptors as part of the oligomerization activation mechanism. Such receptors are, for example, the A-type and B-type PDGF receptors, the EGF-R and HER2/neu, the insulin-R and IGF-1-R. In some cases, heterodimer formation has already been demonstrated [Hammacher et al. (1989), supra; Soos and Siddle (1989), supra]. Molecules comprising the receptor binding domains of ligands for such closely related receptors are specifically within the scope herein.

The term "derivative" is used to define amino acid sequence and glycosylation variants, and covalent modifications of a native ligand.

The term "variant" is used to define amino acid sequence and glycosylation variants of a native ligand.

The terms "native ligand" and "wild-type ligand" are used interchangeably and refer to a ligand amino acid sequence as occurring in nature ("native sequence ligand"), including mature, pre-pro and pro forms of such ligands, purified from natural source, chemically synthesized or recombinantly produced. It will be understood that natural allelic variations exist and can occur among individuals, as demonstrated by one or more amino acid differences in the amino acid sequence of each individual. These allelic variations are specifically within the scope herein.

The terms "amino acid" and "amino acids" refer to all naturally occurring L-α-amino acids. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids
  Acidic Residues: aspartic acid, glutamic acid
  Basic Residues: lysine, arginine, histidine II. Uncharged Amino Acids
  Hydrophilic Residues: serine, threonine, asparagine, glutamine
  Aliphatic Residues: glycine, alanine, valine, leucine, isoleucine
  Non-polar Residues: cysteine, methionine, proline
  Aromatic Residues: phenylalanine, tyrosine, tryptophan The term "amino acid sequence variant" refers to molecules with some differences in their amino acid sequences as compared to a native sequence of a ligand. Ordinarily, the amino acid sequence variants will possess at least about 70% homology with at least one receptor binding domain of a native ligand, and preferably, they will be at least about 80%, more preferably at least about 90% homologous with a receptor binding domain of a native ligand. The amino acid sequence variants possess substitutions, deletions, and/or insertions at certain positions within the amino acid sequence of a native ligand.

"Homology" is defined as the percentage of residues in the candidate amino acid sequence that are identical with the residues in the amino acid sequence of a receptor binding domain of a native ligand after aligning the sequences and introducing gaps, if necessary, to achieve the maximum percent homology. Methods and computer programs for the alignment are well known in the art.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native ligand sequence. Immediately adjacent to an amino acid means connected to either the α-carboxy or α-amino functional group of the amino acid.

Deletional variants are those with one or more amino acids in the native ligand amino acid sequence removed. Ordinarily, deletional variants will have one or two amino acids deleted in a particular region of the molecule.

The term "glycosylation variant" is used to refer to a ligand having a glycosylation profile different from that of a native ligand. Glycosylation of polypeptides is typically either N-linked or O-linked. N-linked refers to the attachment of the carbohydrate moiety to the side-chain of an asparagine residue. The tripeptide sequences, asparagine-x-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. Any difference in the location and/or nature of the carbohydrate moieties present in a ligand as compared to its native counterpart is within the scope herein.

The glycosylation pattern of native ligands can be determined by well known techniques of analytical chemistry, including HPAE chromatography [Hardy, M. R. et al., *Anal. Biochem.* 170, 54–62 (1988)], methylation analysis to determine glycosyl-linkage composition [Lindberg, B., *Meth. Enzymol.* 28. 178–195 (1972); Waeghe, T. J. et al., *Carbohydr. Res.* 123, 281–304 (1983)], NMR spectroscopy, mass spectrometry, etc.

For ease, changes in the glycosylation pattern of a native ligand are usually made at the DNA level, essentially using the techniques discussed hereinabove with respect to the amino acid sequence variants.

Chemical or enzymatic coupling of glycosydes to the ligands of the present invention may also be used to modify or increase the number or profile of carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep., 1987), and in Aplin and Wriston, CRC *Crit. Rev. Biochem.*, pp. 259–306

Carbohydrate moieties present on a ligand may also be removed chemically or enzymatically. Chemical deglycosylation requires exposure to trifluoromethanesulfonic acid or an equivalent compound. This treatment results in the cleavage of most or all sugars, except the linking sugar, while leaving the polypeptide intact. Chemical deglycosylation is described by Hakimuddin et al., *Arch. Biochem. Biophys.* 259, 52 (1987) and by Edge et al., *Anal. Biochem.* 118, 131 (1981). Carbohydrate moieties can be removed by a variety of endo- and exoglycosidases as described by Thotakura et al., *Meth. Enzymol.* 138, 350 (1987). Glycosylation is suppressed by tunicamycin as described by Duskin et al., *J. Biol. Chem.* 257, 3105 (1982). Tunicamycin blocks the formation of protein-N-glycosydase linkages.

Glycosylation variants of the ligands herein can also be produced by selecting appropriate host cells. Yeast, for example, introduce glycosylation which varies significantly from that of mammalian systems. Similarly, mammalian cells having a different species (e.g. hamster, murine, insect, porcine, bovine or ovine) or tissue (e.g. lung, liver, lymphoid, mesenchymal or epidermal) origin than the source of the ligand, are routinely screened for the ability to introduce variant glycosylation.

The terms "ligand variant" and "variant ligand", that are used interchangeably, include both amino acid sequence variants and glycosylation variants of a native ligand.

"Covalent derivatives" include modifications of a native ligand with an organic proteinaceous or non-proteinaceous derivatizing agent, and post-translational modifications. Covalent modifications are traditionally introduced by reacting targeted amino acid residues of the ligand with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-ligand antibodies for immunoaffinity purification of the recombinant glycoprotein. Such modifications are within the ordinary skill in the art and are performed without undue experimentation. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the ligands used in accordance with the present invention. Other post-translational modifications include hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Covalent derivatives specifically include fusion molecules in which ligands of the invention ar covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The ligands may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

Native ligands and derivatives that can activate receptors in accordance with the present invention are well known in the art or can be prepared by art known methods.

The operability of the present invention was first demonstrated with HGFr/HGF or HGF variant receptor/ligand pairs. HGF was identified initially as a mitogen for hepatocytes [Michalopoulos et al., *Cancer Res.* 44, 4414–4419 (1984); Russel et al., *J. Cell. Physiol.* 119, 183–192 (1984) and Nakamura et al., *Biochem. Biophys. Res. Comm.* 122:1450–1459 (1984)]. Nakamura et al., Supra reported the purification of HGF from the serum of partially hepatectomized rats. Subsequently, HGF was purified from rat platelets, and its subunit structure was determined [Nakamura et al., *Proc. Natl. Acad. Sci. USA*, 83, 6489–6493 (1986); and Nakamura et al., *FEBS Letters* 224, 311–316 (1987)]. The purification of human HGF (huHGF) from human plasma was first described by Gohda et al., *J. Clin. Invest.* 81, 414–419 (1988).

Both rat HGF and huHGF have been molecularly cloned, including the cloning and sequencing of a naturally occurring variant lacking 5 amino acids designated "delta5 HGF" [Miyazawa et al., *Biochem. Biophys. Res. Comm.* 163, 967–973 (1989); Nakamura et al., *Nature* 342, 440–443 (1989); Seki et al, *Biochem. and Biophys. Res. Commun.* 172, 321–327 (1990); Tashiro et al., *Proc. Natl. Acad. Sci. USA* 87, 3200–3204 (1990); Okajima et al., *Eur. J. Biochem.* 193, 375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the hHGF cDNA reveals that both the α- and the β-chains are contained in a single open reading frame coding for a pre-pro precursor protein. In the predicted primary structure of mature hHGF, an interchain S—S bridge is formed between Cys 487 of the α-chain and Cys 604 in the δ-chain (see Nakamura et al., *Nature*, supra). The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four Kringle domains. The Kringle 1 domain extends from about aa 128 to about aa 206, the Kringle 2 domain is between about aa 211 and about aa 288, the Kringle 3 domain is defined as extending from about aa 303 to about aa 383, and the Kringle 4 domain extends from about aa 391 to about aa 464 of the α-chain. It will be understood that the definition of the various Kringle domains is based on their homology with kringle-like domains of other proteins (prothrombin, plasminogen), therefore, the above limits are only approximate. As yet, the function of these Kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, hHGF appears to have no proteolytic activity and the precise role of the β-chain remains unknown. HGF contains four putative glycosylation sites, which are located at positions 294 and 402 of the α-chain and at positions 566 and 653 of the β-chain.

In a portion of cDNA isolated from human leukocytes in-frame deletion of 15 base pairs was observed. Transient expression of the cDNA sequence in COS-1 cells revealed that the encoded HGF molecule (delta5 HGF) lacking 5 amino acids in the Kringle 1 domain was fully functional (Seki et al., supra).

A naturally occurring huHGF variant has recently been identified which corresponds to an alternative spliced form of the huHGF transcript containing the coding sequences for the N-terminal finger and first two kringle domains of mature huHGF [Chan et al., Science 254, 1382–1385 (1991); Miyazawa et al., Eur. J. Biochem. 197, 15–22 (1991)]. This variant, designated HGF/NK2, has been proposed to be a competitive antagonist of mature huHGF.

The comparison of the amino acid sequence of rat HGF with that of huHGF revealed that the two sequences are highly conserved and have the same characteristic structural features. The length of the four Kringle domains in rat HGF is exactly the same as in huHGF. Furthermore, the cysteine residues are located in exactly the same positions; an indication of similar three-dimensional structures (Okajima et al., supra; Tashiro et al., supra).

As used herein, the terms "hepatocyte growth factor", "HGF" and "huHGF" refer to a (human) growth factor capable of specific binding to a receptor of wild-type (human) HGF, which growth factor typically has a structure with six domains (finger, Kringle 1, Kringle 2, Kringle 3, Kringle 4 and serine protease domains), but nonetheless may have fewer domains or may have some of its domains repeated if it still retains its qualitative HGF receptor binding ability. This definition specifically includes the delta5 huHGF as disclosed by Seki et al., supra. The terms "hepatocyte growth factor" and "HGF" also include hepatocyte growth factor from any non-human animal species, and in particular rat HGF.

The terms "wild-type human hepatocyte growth factor", "native human hepatocyte growth factor", "wild-type (wt) huHGF", and "native huHGF" refer to native sequence human HGF, i.e., that encoded by the cDNA sequence published by Miyazawa, et al. 1989, supra, or Nakamura et al. , 1989, supra, including its mature, pre, pre-pro, and pro forms, purified from natural source, chemically synthesized or recombinantly produced. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms as defined for the purpose of the present invention. It will be understood that natural allelic variations exist and can occur among individuals, as demonstrated by one or more amino acid differences in the amino acid sequence of each individual. Amino acid positions in the variant huHGF molecules herein are indicated in accordance with the numbering of Miyazawa et al. 1989, supra.

In the course of a recent study of the structure-activity and structure-receptor binding relationship in amino acid sequence variants of HGF, the results of which are disclosed in the examples hereinafter, domains critical for ligand binding and/or activation have been identified in the wild-type HGF amino acid sequence. A number of C-terminal truncations of HGF were made by deleting either the β-chain or the β-chain in addition to a progressive number of kringles. Deletion of the first Kringle (variant ΔK1) of HGF affected biological activity most, showing at least a 100-fold reduction (SA<0.2% of wt rhuHGF). Similarly, binding of this variant was also affected as it failed to compete for binding with wt rhuHGF. Deletion of all other Kringles (variants ΔK2, ΔK3 or ΔK4) also induces severely reduced mitogenic activity. However, the receptor binding affinities (Kds) of these deletion variants remained close to that observed with wt rhuHGF. These data showed that kringles K3 and K4 are not required for receptor binding, and were in agreement with previous observations by Miyazawa et al., 1991 supra and Chan et al., 1991 supra, in the sense that variant N-303, which in amino acid sequence is very similar to HGF/NK2, retains the ability to compete efficiently for binding to the HGF receptor (Kd~280 pM). Furthermore, the observations that N-303 is sufficient to bind to the receptor and that the second kringle is not required for binding the HGF receptor (in the context of the remainder of the molecule) suggest that the receptor binding domain is contained within the finger and first kringle of huHGF.

To elucidate the functional importance of the protease domain of HGF, several single, double and triple mutations were made in order to reconstitute a potential serine-protease active site. The amino acid substitutions were made at positions 534, 673 and 692 of the wild-type hHGF amino acid sequence. In most cases, the biological activity was substantially reduced without substantial decrease in the ligand binding affinity. The biological activity of the double variants Q534H,Y673S and Y673S,V692S and of the triple variant Q534H,Y673S,V692S were less than 3% compared to WT rhuHGF. However, the Kd of these variants was not significantly different from that of the wild-type human HGF molecule. These results indicate that certain mutations within the β-chain of HGF block mitogenic activity but have no significant effect on the receptor binding ability of HGF. Thus, it appears that these mutants are defective in an activity subsequent to receptor binding.

Alterations that potentially increase the receptor binding capacity of HGF are, for example, in the amino acid region corresponding to a potential serine protease active site. This region includes amino acids Q534, Y673 and V692 in the wild-type huHGF amino acid sequence. The replacement of these amino acids with any other amino acid, and preferably with amino acids of different size and/or polarity is believed to further improve the receptor binding properties of the HGF variant.

Additional alterations may be at the C-terminal end and/or in the Kringle domains of the HGF molecule. In addition to the deletion mutants referred to hereinabove, HGF variants with alterations within the Kringle 1 domain are of great interest. As we have found that the receptor binding region is contained within the finger and the Kringle 1 regions of the HGF molecule, amino acid alterations within these domains are expected to significantly alter the receptor binding properties (and the biological activity) of the variants of the present invention. Alterations at residues that are most exposed to the interior in the Kringle structure (mostly charged residues) are particularly likely to cause profound changes in the receptor binding properties and/or biological activity of the HGF variants.

Further ligands for receptors with tyrosine kinase activity are commercially available (e.g. insulin) and/or are characterized by their nucleotide and deduced amino acid sequences. Their biological activities are also known.

EGF and related proteins are known [Carpenter, G. and Cohen, S. Ann. Rev. Biochem. 48, 193–216 (1979); Massanque, J., J. Biol. Chem. 255, 21393–21396 (1990); Gray, A. et al., Nature 303, 722–725 (1983); Bell,G.I. et al., Nucl. Acid. Res. 14, 8427–8446 (1986)].

The amino acids sequence and preparation of human insulin-like growth factors 1 and 2 (IGF-I and IGF-II) is, for example, disclosed in EP 128,733 (published 19 Dec., 1984).

Ligands for HER2/neu (p185$^{HER2}$) have been designated as "heregulin-2" (HRG2) polypeptides, and include HRG2-α and HRG2-β1, -β2 and -β3. The structure, preparation and use of these ligands and their derivatives, including amino acid sequence variants, are disclosed in copending U.S. applications Ser. Nos. 07/705,256 (filed 24 May, 1991 now abandoned); 07/790,801 (filed 8 Nov., 1991 now abandoned); and 07/880,917 (filed 11 May, 1992 now abandoned). The amino acid sequence of HRG shares a number a features with the EGF family of transmembrane bound growth factors. Alignment of the amino acid sequences in the region of the EGF motif and flanking transmembrane domain of several human EGF related proteins shows a relatively great degree of homology with heparin binding EGF-like growth factor (HB-EGF) [Higashiyama et al., *Science* 251, 936–939 (1991); amphiregulin (AR) [Plowman, G. D. et al., *Mol. Cell. Biol.* 10. 1969–1981 (1990)); transforming growth factor-α (TGF-α); EGF [Bell, G. I. et al. (1986), supra]; and schwanoma-derived growth factor [Kimura, H. et al., 348, 257–260 (1990)].

A typical representative of bivalent ligands for receptors with tyrosine kinase activity is platelet derived growth factor (PDGF). PDGF is a major mitogen in serum for connective tissue-derived cells in culture [see Ross, R. et al., *Cell* 46, 155–169 (1986) for review]. It is a 30-kD dimer composed of disulfide-bonded A and B polypeptide chains. All three possible isoforms of the two chains, PDGF-AA, PDGF-AB, and PDGF-BB, have been identified and purified from natural sources [Heldin, C.-H. et al., *Nature* 319, 511–514 (1986); Hammacher, A. et al., *Eur. J. Biochem.* 176, 1790186 (1988); Stroobant, P. and Waterfield, M. D., *EMBO J.* 3, 2963–2967 (1984)]. The different isoforms have been found to differ in functional activities, most likely due to different binding specificities to two separate receptor classes [Nister, M. et al., *Cell* 52, 791–799 (1988); Heldin, C.-H. et al., *EMBO J.* 7, 1387–1393 (1988); Hart, C. E. et al. , *Science* 240, 1529–1531 (1988)]. The A-type PDGF receptor binds all three isoforms f PDGF, whereas the B-type receptor binds PDGF-BB with high affinity and PDGF-AB with lower affinity but does not bind PDGF-AA with any appreciable affinity.

Another bivalent ligand is human growth hormone (hGH). hGH is a member of an homologous hormone family that includes placental lactogens, prolactins, and other genetic and species variants of growth hormone, and is usually referred to as the family of hematopoietins, including pituitary and hematopoietic hormones [Nicoll, C. S. et al., *Endocrine Reviews* 7, 169 (1986)]. The cloned gene for hGH has been expressed in a secreted form in *E. coli* [Chang, C. N. et al., *Gene* 55, 189 (1987)], and its nucleotide and amino acid sequences have been reported [Goeddel et al., *Nature* 281, 544 (1979); Gray et al., *Gene* 39, 247 (1985)]. The three-dimensional folding pattern of porcine growth hormone (pGH) has been reported [Abdel-Meguid, S.S. et al., *Proc. Natl. Acad. Sci. USA* 84 6434 (1987)]. hGH receptor and antibody binding sites have been identified by homolog-scanning mutagenesis [Cunningham, B. et al., *Science* 243, 1330 (1989)]. GH variant with N-terminal truncations or with mutations in the N-terminal region are known [Gertler et al., *Endocrinology* 118, 720 (1986); Ashkenazi, A. et al., *Endocrinology* 121, 414 (1987); and Binder, *Mol. Endo.* 7, 1060–1068 (1990)]. Antagonist variants of hGH were described by Chan et al., *Mol. Endo.* 5, 1845 (1991) and in the references cited therein, and in WO 91/05853. hGH variants are also disclosed by Cunningham et al., *Science* 244, 1081 (1989); and *Science* 243, 1330–1336 (1989).

The structures of several other hematopoietic ligands have been determined recently. Granulocyte-macrophage colony stimulating factor (GM-CSF) and IL-4 are about 60 residues shorter than growth hormone. Both the crystal structure of GM-CSF [Diederichs, K. et al., *Science* 254, 1779–1782 (1991); Walter, M. R. et al., *J. Mol. Biol.* 224, 1075–1085 (1992)], and the NMR structure of IL-4 [Powers, R. et al., *Science* 256, 1673–1677 (1992); Smith, L. J. et al., *J. Mol. Biol.* 224, 899–904 (1992)] reveal the same topology as GH, but with an additional structural motif not seen before: a short segment of B-ribbon formed by residues in the long crossover connections. From the evidence thus far available, it appears that two topologically-conserved receptor-binding sites are a common theme throughout the hematopoietins. Whereas native hGH use these two sites to bind two copies of the same receptor, in many other cases such as IL-2, IL-3, GM-CSF and others, the equivalent segments may form binding interfaces for two different receptor subunits.

Receptor binding domains in a native ligand sequence can be determined by methods known in the art, including X-ray studies, mutational analyses, and antibody binding studies. The mutational approaches include the techniques of random saturation mutagenesis coupled with selection of escape mutants, insertional mutagenesis, and homolog-scanning mutagenesis (replacement of sequences from human ligands, which bind the corresponding receptor, with unconserved sequences of a corresponding ligand from another animal species, e.g. mouse, which do not bind the human receptor). Another strategy suitable for identifying receptor-binding domains in ligands is known as alanine-scanning mutagenesis [ALA-scan, Cunningham and Wells, *Science* 244, 1081–1985 (1989)]. This method involves the identification of regions that contain charged amino acid side chains. The charged residues in each region identified (i.e. Arg, Asp, His, Lys, and Glu) are replaced (one region per mutant molecule) with alanine and the receptor binding of the obtained ligands is tested, to assess the importance of the particular region in receptor binding. Another method for identifying active domains in polypeptides along with a number of hGH variants is disclosed in WO 90/04788 (published 3 May, 1990). According to this method, the active domains (e.g. receptor binding domains) in a polypeptide are determined by substituting selected amino acid segments of the polypeptide with an analogous polypeptide segment from an analog of the polypeptide which has a different activity with the target substance (e.g. receptor) as compared to the parent polypeptide. A further powerful method for the localization of receptor binding domain(s) in a ligand is through the use of neutralizing (blocking) monoclonal antibodies (MAbs). Usually a combination of these and similar methods is used for localizing the domains important for receptor binding.

Derivatives, such as amino acid sequence variants, of the foregoing and other ligands for receptors that require oligomerization for activation of receptor function are also known or can be easily prepared by methods known in the art, such as by site directed mutagenesis of the DNA encoding the precursor or parental ligand, thereby producing DNA encoding the variant. Modifications of the DNA encoding the variant ligand molecules must not place the sequence out of reading frame, and preferably will not create complementary regions which could produce secondary mRNA structure. The DNA encoding the variant ligand is inserted into an appropriate expression vector, and suitable host cells are then transfected with this DNA. Culturing the host cells in an appropriate medium will result in the production of polypeptides encoded by the DNA, and secretion of the polypeptide into the host cell culture medium. These techniques will be described in more detail hereinbelow.

Alternatively, amino acid variants of native ligand molecules are prepared by in vitro synthesis using standard solid-phase peptide synthesis procedures as described by Merrifield (J. Am. Chem. Soc. 85:2149 [1963]), although other equivalent chemical syntheses known in the art may be used. Solid-phase synthesis is initiated from the C-terminus of the peptide by coupling a protected α-amino acid to a suitable resin. The amino acids are coupled to the peptide chain using techniques well known in the art for the formation of peptide bonds.

Glycosylation variants of native ligand molecules may be prepared by techniques known in the art. Chemical and enzymatic coupling of glycosides to proteins can be accomplished using a variety of activated groups, for example, as described by Alpin and Wriston in CRC Crit. Rev. Biochem. pp. 259–306 (1981). The advantages of the chemical coupling techniques are that they are relatively simple and do not need the complicated enzymatic machinery required for natural O- and N-linked glycosylation. Depending on the coupling mode used, the sugar(s) may be attached to (a) arginine and histidine, (b) free carboxyl groups such as those of glutamic acid and aspartic acid, (c) free sulfhydryl groups such as those of cysteine, (d) free hydroxyl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep., 1987). Carbohydrates present in a native ligand molecule can, for example, be removed by the use of an endoglycosidase, such as Endoglycosydase H (Endo-H), which is capable of (partial) removal of high mannose and hybrid oligosaccharides. This treatment is accomplished via techniques known per se, for example, according to the method of Tarentino et al., J. Biol. Chem. 249, 811 (1974), Trimble et al., Anal. Biochem. 141, 515 (1984) and Little et al., Biochem. 23, 6191 (1984). More preferably, glycosylation variants of ligands are made by appropriate mutations at the DNA level, to provide a protein with the desired, altered glycosylation pattern.

In accordance with the present invention, a first and a second ligand (which may be identical or different) may be directly fused to each other. Such fusion molecules can be prepared by expression of the encoding DNA sequence in a suitable microorganism or cell culture, employing standard techniques of recombinant DNA technology. Alternatively, they may be obtained by chemical synthesis.

The term "heterologous linker" is used to refer to any organic or inorganic linker molecules coupling two ligands (as hereinabove defined), provided that they are different from a linker connecting the two ligands in their native environment, e.g. in a bivalent ligand. Should the two ligands be connected in their native environment with an amino acid sequence, variants encoded by a DNA sequence capable of hybridizing under stringent conditions with the DNA sequence encoding such connecting amino acid sequence are specifically excluded from the definition of the term "heterologous linker".

"Stringent conditions" are overnight incubation at 37° C. in a solution comprising: 40% formamide, 5×SSC (150 mM NaCl, 15 mM trisodium citrate), 50 mM sodium phosphate (pH 7.6), 5 ×Denhardt's solution, 10% dextrane sulfate, and 20 μg/ml denatured, sheared salmon sperm DNA, followed by washing the filters in 1×SSC at about 50° C.

In a preferred embodiment, the linker comprises an immunoglobulin sequence.

The term "immunoglobulin" generally refers to polypeptides comprising a light or heavy chain usually both disulfide bonded in the native "Y" configuration, although other linkage between them, including tetramers or aggregates thereof, is within the scope hereof.

Immunoglobulins (Ig) and certain variants thereof are known and many have been prepared in recombinant cell culture. For example, see U.S. Pat. No. 4,745,055; EP 256,654; Faulkner et al., Nature 298:286 (1982); EP 120, 694; EP 125,023; Morrison, J. Immun. 123:793 (1979); Köhler et al., Proc. Nat'l. Acad. Sci. USA 77:2197 (1980); Raso et al. , Cancer Res. 41:2073 (1981); Morrison et al., Ann. Rev. Immunol. 2:239 (1984); Morrison, Science 229:1202 (1985); Morrison et al., Proc. Nat'l. Acad. Sci. USA 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein. The immunoglobulin moiety in the chimeras of the present invention may be obtained from IgG-1, IgG-2, IgG-3 or IgG-4 subtypes, IgA, IgE, IgD or IgM, but preferably IgG-1 or IgG-3.

Chimeras constructed from a receptor sequence linked to an appropriate immunoglobulin constant domain sequence (immunoadhesins) are known in the art. Immunoadhesins reported in the literature include fusions of the T cell receptor [Gascoigne et al., Proc. Natl.Acad. Sci. USA 84, 2936–2940 (1987)]; CD4* [Capon et al., Nature 337, 525–531 (1989); Traunecker et al., Nature 339, 68–70 (1989); Zettmeissl et al., DNA Cell Biol. USA 9, 347–353 (1990); Byrn et al., Nature 344, 667–670 (1990)]; L-selectin (homing receptor) [Watson et al., J. Cell. Biol. 110, 2221–2229 (1990); Watson et al., Nature 349, 164–167 (1991)]; CD44* [Aruffo et al., Cell 61, 1303–1313 (1990)]; CD28 * and B7* [Linsley et al., J. Exp. Med. 173, 721–730 (1991)]; CTLA-4* [Lisley et al., J. Exp. Med. 174, 561–569 (1991)]; CD22* [Stamenkovic et al., Cell 66. 1133–1144 (1991)]; TNF receptor [Ashkenazi et al., Proc. Natl. Acad. Sci. USA 88, 10535–10539 (1991); Lesslauer et al., Eur. J. Immunol. 27, 2883–2886 (1991); Peppel et al ., J. Exp. Med. 174, 1483–1489 (1991)]; NP receptors [Bennett et al., J. Biol. Chem. 266, 23060–23067 (1991)]; IgE receptor α-chain [Ridgway and Gorman, J. Cell. Biol. 115, abstr. 1448 (1991)]; HGF receptor (Mark, M. R. et al., 1992, J. Biol. Chem. submitted], where the asterisk (*) indicates that the receptor is member of the immunoglobulin superfamily. These immunoadhesins were manufactured with different goals in mind, they are, however, all common in that they can possess many of the desired chemical and biological properties of human antibodies.

Ligand-immunoglobulin chimeras are disclosed in copending applications Ser. Nos. 07/834,902 filed 13 Feb., 1992 U.S. Pat. No. 5,304,6(for L-selectin ligands); 07/884, 811 U.S. Pat. No. 5,316,921, and 07/885,971 U.S. Pat. No. 5,328,837, both filed 18 May, 1992 (for HGF variants). These chimeras can be made in a similar way to the construction of receptor-immunoglobulin chimeras.

Ordinarily, the ligand is fused C-terminally to the N-terminus of the constant region of an immunoglobulin in place of the variable region(s), however N-terminal fusions of the selectin variants are also desirable.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, however, the ligand-immunoglobulin chimeras of this invention may be synthesized according to known methods.

The precise site at which the fusion is made is not critical; particular sites are well known and may be selected in order to optimize the biological activity, secretion or binding characteristics of the ligand-immunoglobulin chimeras.

In some embodiments, the hybrid immunoglobulins are assembled as monomers, or hetero- or homo-multimers, and particularly as dimers or tetramers, essentially as illustrated in WO 91/08298.

In a preferred embodiment, the C-terminus of a ligand sequence which contains the binding site(s) for a receptor, is fused to the N-terminus of the C-terminal portion of an antibody (in particular the Fc domain), containing the effector functions of an immunoglobulin, e.g. immunoglobulin $G_1$ (IgG-1). It is possible to fuse the entire heavy chain constant region to the sequence containing the receptor binding site(s). However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins) is used in the fusion. In a particularly preferred embodiment, the amino acid sequence containing the receptor binding site(s) is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation.

In some embodiments, the ligand-immunoglobulin chimeras are assembled as hetero-multimers, and particularly as hetero-dimers or -tetramers. Generally, these assembled immunoglobulins will have known unit structures. A basic four chain structural unit is the form in which IgG, IgD, and IgE exist. A four-chain unit is repeated in the higher molecular weight immunoglobulins; IgM generally exists as a pentamer of basic four-chain units held together by disulfide bonds. IgA globulin, and occasionally IgG globulin, may also exist in multimeric form in serum. In the case of multimer, each four-chain unit may be the same or different.

Various exemplary assembled ligand-immunoglobulin chimeras within the scope herein are schematically diagrammed below:
(a) $AC_L$—$AC_L$;
(b) $AC_H$-[$AC_H$, $AC_L$-$AC_H$, $AC_L$-$V_HC_H$, or $V_LC_L$-$AC_H$];
(c) $AC_L$-$AC_H$-[$AC_L$-$AC_H$, $AC_L$-$V_HC_H$, $V_LC_L$-$AC_H$, or $V_LC_L$-$V_HC_H$];
(d) $AC_L$-$V_HC_H$-[$AC_H$, or $AC_L$-$V_HC_H$, or $V_LC_L$-$AC_H$];
(e) $V_LC_L$-$AC_H$-[$AC_L$-$V_HC_H$, or $V_LC_L$-$AC_H$]; and
(f) $[A$-$Y]_n$-$[V_LC_L$-$V_HC_H]_2$,
wherein
each A represents identical or different amino acid sequences capable of selective binding to said receptor;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.
In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the ligand sequences of the present invention can be inserted between immunoglobulin heavy chain and light chain sequences such that an immunoglobulin comprising a chimeric heavy chain is obtained. In this embodiment, the ligand sequences are fused to the 3' end of an immunoglobulin heavy chain in each arm of an immunoglobulin, either between the hinge and the CH2 domain, or between the CH2 and CH3 domains. Similar constructs have been reported by Hoogenboom, H. R. et al., *Mol. Immunol.* 28, 1027–1037 (1991).

The ligand-immunoglobulin chimeras of the present invention are constructed in a fashion similar to the construction of bispecific antibodies, such as, for example, disclosed in EP 125,023 (published 14 Nov., 1984); U.S. Pat. No. 4,444,878 (issued 24 Apr., 1984); Munro, A,, *Nature* 312, 597 (1984); Morrison, et al., *Science* 229, 1202–1207 (1985); Berg et al., *Proc. Natl. Acad. Sci. USA* 88, 4723–4727 (1991)].

The DNA encoding a native ligand herein may be obtained from any cDNA library prepared from tissue believed to possess mRNA for the desired ligand and to express it at a detectable level. Libraries are screened with probes designed to identify the gene of interest or the protein encoded by it. For cDNA expression libraries, suitable probes usually include mono- and polyclonal antibodies that recognize and specifically bind to the desired protein; oligonucleotides of about 20–80 bases in length that encode known or suspected portions of the ligand cDNA from the same or different species; and/or complementary or homologous cDNAs or their fragments that encode the same or similar gene.

An alternative means to isolate the gene encoding a desired native ligand is to use polymerase chain reaction (PCR) methodology as described in U.S. Pat. No. 4,683,195, issued 28 Jul., 1987, in section 14 of Sambrook et al., *Molecular Cloning: A Laboratory Manual*, second edition, Cold Spring Harbor Laboratory Press. New York, 1989, or in Chapter 15 of *Current Protocols in Molecular Biology*, Ausubel et al. eds., Greene Publishing Associates and Wiley-Interscience 1991.

Another alternative is to chemically synthesize the gene encoding the desired (native or variant) ligand using one of the methods described in Engels et al., *Agnew. Chem. Int. Ed. Engl.* 28, 716 (1989). These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or, alternatively, if the target amino acid sequence is known, one may infer potential nucleic acid sequences, using known and preferred coding residues for each amino acid residue.

The amino acid sequence variants of the ligands of this invention are preferably constructed by mutating the DNA sequence that encodes the protein core of a wild-type ligand. Generally, particular regions or sites of the DNA, identified by methods discussed hereinabove, will be targeted for mutagenesis, and thus the general methodology employed to accomplish this is termed site-directed mutagenesis. The mutations are made using DNA modifying enzymes such as restriction endonucleases (which cleave DNA at particular locations), nucleases (which degrade DNA) and/or polymerases (which synthesize DNA).

The following is a brief discussion of certain commonly used techniques of recombinant DNA technology that can be used for making the ligand dimers of the present invention. These and similar techniques are equally suitable for making variants of receptor binding domains of native ligands, fusions of native and variant ligands, with or without a linker, including linkers of immunoglobulin origin. Further details of these and similar techniques are found in general textbooks, such as, for example, Sambrook et al., supra, and *Current Protocols in Molecular Biology*, Ausubel et al. eds., supra.

Site Directed Mutagenesis

Preparation of ligand variants and of dimers including such ligand variants in accordance herewith is preferably achieved by site-specific mutagenesis of DNA that encodes an earlier prepared variant or a nonvariant version of the protein. Site-specific mutagenesis allows the production of variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., *DNA*, 2: 183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Veira et al., *Meth. Enzymol.*, 153: 3 (1987)] may be employed to obtain single-stranded DNA.

In general, site-directed mutagenesis may, for example, be performed by first obtaining a single-stranded vector that includes within its sequence a DNA sequence that encodes the relevant selectin. An oligonucleotide primer bearing the desired mutated sequence is prepared, generally synthetically, for example, by the method of Crea et al., *Proc. Natl. Acad. Sci.* (USA), 75: 5765 (1978). This primer is then annealed with the single-stranded ligand sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected, via hybridization to a radioactive probe consisting of the $^{32}$P-labeled mutagenesis primer, that include recombinant vectors bearing the mutated sequence arrangement.

After such a clone is selected, the mutated region may be removed and placed in an appropriate vector for the production of the desired variant, generally an expression vector of the type that typically is employed for transformation of an appropriate eukaryotic host. In the context of the present invention, Chinese hamster ovary (CHO) cells or 293 (human kidney cells described by Graham et al., *J. Gen. Virol.*, 36: 59 (1977)) are preferred for the preparation of long-term stable polypeptide producers. However, the invention is not limited to CHO production, as it is known that numerous other cell types are suitably employed, particularly where one desires only transient production of the enzyme for test purposes. For example, described below is a transient system employing 293 cells that provides a convenient system for production of ligand variants or ligand dimers, e.g. ligand-immunoglobulin chimeras for analytical purposes.

Another method for making mutations in the DNA sequence encoding a ligand involves cleaving the DNA at the appropriate position by digestion with restriction enzymes, recovering the properly cleaved DNA, synthesizing an oligonucleotide encoding the desired amino acid and flanking regions such as polylinkers with blunt ends (or, instead of using polylinkers, digesting the synthetic oligonucleotide with the restriction enzymes also used to cleave the ligand-encoding DNA, thereby creating cohesive termini), and ligating the synthetic DNA into the remainder of the ligand-encoding structural gene.

PCR Mutagenesis

PCR mutagenesis is also suitable for making ligands, including ligand dimers for practicing the present invention. While the following discussion refers to DNA, it is understood that the technique also find application with RNA. The PCR technique generally refers to the following procedure. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more)-part ligation.

Host Cell Cultures and Vectors

Although expression on Chinese hamster ovary (CHO) cells and in the human embryonic kidney cell line 293 [Urlaub and Chasin, *Proc. Natl. Acad. Sci. USA* 77, 4216 (1980); Graham et al., *J. Gen. Virol.*, 36, 59 (1977)] are ultimately preferred, the vectors and methods disclosed herein are suitable for use in host cells over a wide range of eukaryotic organisms.

In general, prokaryotes are preferred for the initial cloning of DNA sequences and constructing the vectors useful in the invention. For example, *E. coli* K12 strain 294 (ATCC No. 31,446) and *E. coli* strain W3110 (ATCC No. 27,325) are particularly useful. Other suitable microbial strains include *E. coli* strains such as *E. coli* B, and *E. coli* X1776 (ATCC No. 31,537). These examples are, of course, intended to be illustrative rather than limiting.

Prokaryotes also are useful for expression. The aforementioned strains, as well as bacilli such as *Bacillus subtilis*, and other enterobacteriaceae such as, e.g., *Salmonella typhimurium* or *Serratia marcesans*, and various Pseudomonas species are examples of useful hosts for expression.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include β-lactamase (penicillinase) and lactose promoter systems (Chang et al., *Nature*, 375: 615 (1978); Itakura et al., *Science*, 198: 1056 (1977); Goeddel et al., *Nature*, 281: 544 (1979)) and a tryptophan (trp) promoter system (Goeddel et al., *Nucl. Acids Res.*, 8: 4057 (1980); EPO Appl. Publ. No. 36,776), and the alkaline phosphatase systems. While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell*, 20: 269 (1980)).

In addition to prokaryotes, eukaryotic microbes, such as yeasts, also are suitably used herein. *Saccharomyces cerevisiae*, or common baker's yeast, is the most commonly used among eukaryotic microorganisms, although a number of other strains are commonly available. For example, for expression in Saccharomyces, the plasmid YRp7 (Stinchcomb et al., *Nature*, 282: 39 (1979); Kingsman et al., *Gene*, 7: 141 (1979); Tschemper et al., *Gene*, 10: 157 (1980)) is commonly used. This plasmid already contains the trp1 gene that provides a selection marker for a mutant strain of yeast lacking the ability to grow in tryptophan, for example, ATCC No. 44,076 or PEP4-1 (Jones, *Genetics*, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); Holland et al., *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, CHO cell lines, and W138, BHK, COS-7, (ATCC CRL 1651), 293, and MDCK (ATCC CCL 34) cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al., *Nature*, 273: 113 (1978)). Smaller or larger SV40 fragments are also suitably used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication typically is provided either by construction of the vector to include an exogenous origin, such as may be derived from SV40 or other viral (e.g., Polyoma, Adeno, VSV, BPV) source, or by the host cell chromosomal replication mechanism. If the vector is integrated into the host cell chromosome, the latter is often sufficient.

Satisfactory amounts of ligand variants or dimers are produced by cell cultures; however, refinements, using a secondary coding sequence, serve to enhance production levels even further. The secondary coding sequence comprises dihydrofolate reductase (DHFR) that is affected by an externally controlled parameter, such as methotrexate (MTX), thus permitting control of expression by control of the MTX concentration.

In the selection of a preferred host cell for transfection by the vectors of the invention that comprise DNA sequences encoding both variant selectin and DHFR protein, it is appropriate to consider the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the CHO cell line deficient in DHFR activity, prepared and propagated, as described by Urlaub and Chasin, *Proc. Natl. Acad. Sci.* (USA) 77: 4216 (1980).

On the other hand, if DHFR protein with low binding affinity for MTX is used as the controlling sequence, it is not necessary to use DHFR-deficient cells. Because the mutant DHFR is resistant to MTX, MTX-containing media can be used as a means of selection, provided that the host cells are themselves MTX sensitive. Most eukaryotic cells that are capable of absorbing MTX appear to be sensitive to MTX. One such useful cell line is a CHO line, CHO-K1 (ATCC No. CCL 61).

Typical Cloning and Expression Methodologies Available

If mammalian cells are used as host cells, transfection generally is carried out by the calcium phosphate precipitation method as described by Graham and Van der Eb, *Virology*, 52: 546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci. U.S.A.*, 75: 1929–1933 (1978).

If prokaryotic cells or cells that contain substantial cell wall constructions are used, the preferred method of transfection is calcium treatment using calcium as described by Cohen et al., *Proc. Natl. Acad. Sci.* (USA) 69: 2110 (1972), or more recently electroporation.

Construction of suitable vectors containing the desired coding and control sequences employs standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments is used with about 1 unit of enzyme in about 20 μl of buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of the Klenow fragment of DNA Polymerase I (Klenow), phenol-chloroform extracted, and ethanol precipitated.

Size separation of the cleaved fragments is performed using 6 percent polyacrylamide gel described by Goeddel et al., *Nucleic Acids Res.*, 8: 4057 (1980).

For ligation, approximately equimolar amounts of the desired components, suitably end tailored to provide correct matching, are treated with about 10 units T4 DNA ligase per 0.5 μg DNA. (When cleaved vectors are used as components, it may be useful to prevent religation of the cleaved vector by pretreatment with bacterial alkaline phosphatase.)

As discussed above, ligand variants are preferably produced by means of specific mutation. Variants useful in the practice of the present invention are formed most readily through the use of specific oligonucleotide sequences that encode the DNA sequence of the desired mutation, as well as a sufficient number of adjacent nucleotides, to provide a sequence of sufficient size and sequence complexity to form a stable duplex on both sides of the mutation being traversed.

For analysis to confirm correct sequences in plasmids constructed, the ligation mixtures are typically used to transform *E. coli* K12 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9: 309 (1981) or by the method of Maxam et al., *Methods of Enzymology*, 65: 499 (1980).

After introduction of the DNA into the mammalian cell host and selection in medium for stable transformants, amplification of DHFR-protein-coding sequences is effected by growing host cell cultures in the presence of approximately 20,000–500,000 nM concentrations of MTX, a competitive inhibitor of DHFR activity. The effective range of concentration is highly dependent, of course, upon the nature of the DHFR gene and protein and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

In a particular embodiment, ligand-immunoglobulin chimeric molecules are used in accordance with the present invention. The ligand-immunoglobulin chimeras preferably are recovered from the culture medium as a secreted protein, although it also may be recovered from host cell lysates when directly expressed without a secretory signal. When the chimera is expressed in a recombinant cell other than one of human origin, the variant is thus completely free of proteins of human origin. However, it is necessary to purify the variant from recombinant cell proteins in order to obtain preparations that are substantially homogeneous as to protein. As a first step, the culture medium or lysate is centrifuged to remove particulate cell debris.

The chimera is then purified from contaminant soluble proteins, for example, by an appropriate combination of conventional chromatography methods, e.g. gel filtration, ion-exchange, hydrophobic interaction, affinity, immunoaffinity chromatography, reverse phase HPLC; precipitation, e.g. ethanol precipitation, ammonium sulfate precipitation, or, preferably, immunoprecipitation with anti-HGF (polyclonal or monoclonal) antibodies covalently linked to Sepharose. Due to its high affinity to heparin, HGF can be conveniently purified on a heparin, such as heparin-Sepharose column. One skilled in the art will appreciate that purification methods suitable for native HGF may require modification to account for changes in the character of HGF or its variants upon expression in recombinant cell culture.

In a further embodiment, the two (identical or different) ligands are linked with a non-immunoglobulin linker. The linker may be the residue of a covalent cross-linking agent capable of linking the two ligands without the impairment of the receptor binding function or a linkage the formation of which is induced by such cross-linking agents. A concise review of covalent cross-linking reagents, including a guide to the selection of such reagents and methods for their preparation are provided by Tae, H. Jr. in *Meth. Enzymol.* 580–609 (1983) and in the references cited therein. The selection of the most appropriate reagent for a specific purpose from the wide variety of cross-linking agents available, is well within the skill of an ordinary artisan.

In general, zero-length, homo- or heterobifunctional cross-linking agents are preferred for the purpose of the present invention. Zero-length cross linking reagents induce the direct conjugation of two ligands without the introduction of any extrinsic material. Agents that catalyze the formation of disulfide bonds belong in this category. Another example is reagents that induce the condensation of carboxy and primary amino groups to form an amide bond, such as carbodiimides, ethylchloroformate, Woodward's reagent K1, carbonyldiimidazole, etc. Homobifunctional reagents carry two identical functional groups, whereas heterobifunctional reagents contain two dissimilar functional groups. A vast majority of the heterobifunctional cross-linking agents contains a primary amine-reactive group and a thiol-reactive group. A novel heterobifunctional linker for formyl to thiol coupling was disclosed by Heindel, N. D. et al., *Bioconjugate Chem.* 2, 427–430 (1991)]. In a preferred embodiment, the covalent cross-linking agents are selected from reagents capable of forming disulfide (—S—S—), glycol (—CH[OH]—CH[OH]—), azo (—N=N—), sulfone (—S[=$O_2$]—), or ester (—C[=O]—O—) bridges.

In a different approach, the ligands are linked via their oligosaccharides. Chemical or enzymatic oxidation of oligosaccharides on polypeptide ligands to aldehydes yields unique functional groups on the molecule, which can react with compounds containing, for example, amines hydrazines, hydrazides, or semicarbazides. Since the glycosylations sites are well defined in polypeptide molecules, selective coupling via oxidized oligosaccharide moieties will yield in a more uniform product than other coupling methods, and is expected to have less adverse effect on the receptor binding properties of the ligands. Carbohydrate-directed heterobifunctional cross-linking agents are, for example, disclosed in copending patent application Ser. No. 07/926,077 filed 5 Aug., 1992, U.S. Pat. No. 5,329,028.

It will be understood that the coupling of more than two ligand sequences with various linked sequences, e.g., cross-linking reagents is possible, and is within the scope of the present invention.

In a further embodiment, two or more ligands are connected by polypeptide linker sequences, and accordingly, are presented to their receptor as a single-chain multifunctional polypeptide molecule. The polypeptide linker functions as a "spacer" whose function is to separate the functional ligand domains so that they can independently assume their proper tertiary conformation. The polypeptide linker usually comprises between about 5 and about 25 residues, and preferably contains at least about 10, more preferably at least about 15 amino acids, and is composed of amino acid residues which together provide a hydrophilic, relatively unstructured region. Linking amino acid sequences with little or no secondary structure work well. If desired, one or more unique cleavage sites recognizable by a specific cleavage agent (e.g. protease) may be included in the polypeptide linker. The specific amino acids in the spacer can vary, however, cysteines should be avoided. The spacer sequence may mimic the tertiary structure of an amino acid sequence normally linking two receptor binding domains in a native bifunctional ligand. It can also be designed to assume a desired structure, such as a helical structure. Suitable polypeptide linkers are, for example, disclosed in Wo 88/09344 (published 1 Dec., 1988), as are methods for the production of multifunctional proteins comprising such linkers.

In a further specific embodiment, the ligands are dimerized by amphiphilic helices. It is known that recurring copies of the amino acid leucine (Leu) in gene regulatory proteins can serve as teeth that "zip" two protein molecules together to provide a dimer. Leucine zipper was first discovered when a small segment of the protein C/EBP was fit into a hypothetical alpha helix. Surprisingly, the leucines, which make up every seventh amino acid in this protein, lined up in a column. Subsequently, two additional, C/EBP related proteins were identified and shown to have a similar function. One of them, GCN4 is a gene regulatory protein from yeast, the other one, is the product of a proto-oncogene jun. It has been found that zipper regions associate in parallel when they combine, i.e. the leucines on apposed molecules line up side by side. It has also been shown that non-identical proteins may be zippered to provide heterodimers. Such leucine zippers are particularly suitable for preparing ligand dimers within the scope of the invention. Alternatively, the sequence of the amphipathic helix may be taken from a four-helix bundle design, essentially as described by Pack P. and Pluckthun, A., *Biochemistry* 31, 1579–1584 (1992). For further details about molecular, e.g. leucine zippers, which can serve as heterologous linkers for the purpose of the present invention, see for example: Landshculz, W. H., et al. *Science* 240, 1759–1764 (1988); O'Shea, E. K. et al., *Science* 243, 538–542 (1989); McKnight, S. L., *Scientific American* 54–64, April 1991; Schmidt-Dorr. T. et al., *Biochemistry* 30, 9657–9664 (1991); Blondel, A. and Bedouelle, H. *Protein Engineering* 4, 457–461 (1991), Pack, P. and Pluckthun, A., supra, and the references cited in these papers.

In a specific embodiment, the present invention provides methods for the conversion of ligand variants capable of binding their receptors but having no or diminished receptor activating ability to potent agonist of the respective native ligands. The target ligands preferably retain substantially full receptor binding affinity of the native ligand.

The expression "retain substantially full receptor binding affinity of native ligand" and grammatical variant thereof as used herein mean that the receptor binding affinity of the ligand variant is not less then about 70%, preferably not less than about 80%, more preferably not less than about 90%, most preferably not less than about 95% of the affinity with which the corresponding native ligand binds its receptor.

Receptor binding can be determined in standard assays, such as, for example, in the competitive binding assay disclosed in the examples.

The terms "substantially incapable of receptor activation", and "substantially devoid of biological activity" mean that the activity exhibited by a variant ligand is less than about 20%, preferably less than about 15%, more preferably less than about 10%, most preferably less than about 5% of the respective activity of the corresponding native ligand in an established assay of receptor activation or ligand biological activity.

The operability of the present invention was first demonstrated by activating the receptor for hepatocyte growth factor (HGFr) with chimeric molecules formed by the fusion of wild-type HGF ligands and their amino acid sequence variants to immunoglobulin constant domain sequences.

The HGF biological activity may, for example, be determined in an in vitro or in vivo assay of hepatocyte growth promotion. Adult rat hepatocytes in primary culture have been extensively used to search for factors that regulate hepatocyte proliferation. Accordingly, the mitogenic effect of an HGF variant can be conveniently determined in an assay suitable for testing the ability of an HGF molecule to induce DNA synthesis of rat hepatocytes in primary cultures, such as, for example, described in Example 2. Human hepatocytes are also available from whole liver perfusion of organs deemed unacceptable for transplantation, pare-downs of adult livers used for transplantation in children, fetal livers and liver remnants removed at surgery for other indications. Human hepatocytes can be cultured similarly to the methods established for preparing primary cultures of normal rat hepatocytes. Hepatocyte DNA synthesis can, for example, be assayed by measuring incorporation of [$^3$H]thymidine into DNA, with appropriate hydroxyurea controls for replicative synthesis.

The effect of HGF variants on hepatocyte growth can also be tested in vivo in animal models of liver dysfunction and regeneration, such as in rats following partial hepatectomy, or carbon tetrachloride caused hepatic injury, in D-galactosamine induced acute liver failure models, etc. According to a suitable protocol, a liver poison, e.g. α-naphthylisothiocyanate (ANIT) is administered to rats in a predetermined concentration capable of causing reproducible significant elevation of liver enzyme and bilirubin levels. The rats are then treated with the HGF variant to be tested, sacrificed and the liver enzyme and bilirubin levels are determined. The livers are additionally observed for hepatic lesions.

The biological activity of other ligands and ligand variants can be assayed by methods known in the art.

The compounds of the present invention are able to activate their respective receptors and thereby mimic the biological activity of the corresponding native ligands. They can be formulated according to known methods to prepare pharmaceutically useful compositions, whereby the linked ligand variants are combined in admixture with a pharmaceutically acceptable carrier. Suitable carriers and their formulations are described in *Remington's Pharmaceutical Sciences*, 16th ed., 1980, Mack Publishing Co., edited by Oslo et al., specifically incorporated by reference. These compositions will typically contain an effective amount of the compound, for example, from on the order of about 0.5 to about 10 mg/ml, together with a suitable amount of carrier to prepare pharmaceutically acceptable compositions suitable for effective administration to the patient. The compounds may be administered parenterally or by other methods that ensure its delivery to the bloodstream in an effective form, essentially following routes of administration known for the corresponding native ligands.

Compositions particularly well suited for the clinical administration of the compounds o the present invention are the same as or can be developed based upon formulations known for the corresponding native ligands.

Dosages and desired drug concentrations of pharmaceutical compositions may vary depending on the particular use envisioned. Preliminary dosages can be determined in animal tests, and interspecies scaling of dosages can be performed in a manner known in the art, e.g. as disclosed in Mordenti et al., *Pharmaceut. Res.* 8, 1351 (1991) and in the references cited therein.

The following examples merely illustrate the best mode now contemplated for practicing the invention, but should not be construed to limit the invention.

EXAMPLE 1

Recombinant Production of the huHGF Variants
A. Site-directed mutagenesis

Plasmid DNA isolation, polyacrylamide and agarose gel electrophoresis were performed as disclosed in Sambrook et al., supra.

Mammalian expression plasmid pRK 5.1 with a CMV promotor (Genentech, Inc.) was used for mutagenesis of huHGF allowing secretion of the HGF variants in the culture medium and directly assayed for biological activity and binding. This expression vector is a derivative of pRK5, the construction of which is disclosed in EP 307,247 published 15 Mar., 1989. pRK5.1 was derived from RK5 by insertion of the self-complementary oligonucleotide 5'-AGCTTGCCTCGAGGCA-3' (SEQ. ID. NO: 14). The nucleotide sequence encoding this the pRK 5.1 vector is disclosed in copending application Ser. No. 07/885,971 filed 18 May, 1992, U.S. Pat. No. 5,328,837.

The huHGF cDNA used corresponds to the 728 amino acid form as published earlier (Miyazawa et al., 1989, supra).

Mutagenesis was performed according to the method of Kunkel using the commercially available dut- ung- strain of *E. coli* [Kunkel et al., *Method. Enzymol.* 154, 367–382 (1987)]. Synthetic oligonucleotides used for in vitro mutagenesis and sequencing primers were prepared using the Applied Biosystem 380A DNA synthesizer as described [Matteucci et al., *J. Am. Chem. Soc.* 103, 3185–3191 (1981) ]. For generation of the desired mutants, oligonucleotides of sequences coding for the desired amino acid substitutions were synthesized and used as primers. The oligonucleotides were annealed to single-stranded pRK 5.1-huHSA that had been prepared by standard procedures [Viera et al., *Method. Enzymol.* 142, 3 (1987)].

A mixture of three deoxyribonucleotides, deoxyriboadenosine (dATP), deoxyriboguanosine (dGTP), and deoxyribothymidine (dTTP), was combined with a modified thiodeoxyribonuleosine called dCTP(aS) provided in the kit by the manufacturer, and added to the single stranded pRK 5.1-huHGF to which was annealed the oligonucleotide.

Upon addition of DNA polymerase to this mixture, a strand of DNA identical to pRK 5.1-huHGF except for the mutated bases was generated. In addition, this new strand of DNA contained dCTP(aS) instead of dCTP, which served to protect from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule hat was only partly single-stranded. A complete double-stranded DNA homoduplex molecule was then formed by DNA polymerase in the presence of all four deoxyribonucleotide triphosphates, ATP, and DNA ligase.

The following oligonucleotides were prepared to use as primers to generate pRK 5.1-huHGF variant molecules:

| | | |
|---|---|---|
| R494E huHGF: | TTGGAATCCCATTTACAACCTCGAGTTGTTTCGTTTTGGCACAAGAT | (SEQ. ID. NO: 1) |
| R494D huHGF: | GAATCCCATTTACGACGTCCAATTGTTTCG | (SEQ. ID. NO: 2) |
| R494A huHGF: | CCCATTTACAACTGCCAATTGTTTCG | (SEQ. ID. NO: 3) |

-continued

| | | |
|---|---|---|
| Q534H huHGF: | AGAAGGGAAACAGTGTCGTGCA | (SEQ. ID. NO: 4) |
| Y673S huHGF: | AGTGGGCCACCAGAATCCCCCT | (SEQ. ID. NO: 5) |
| V692S huHGF: | TCCACGACCAGGAGAAATGACAC | (SEQ. ID. NO: 6) |
| ΔK1 huHGF: | GCATTCAACTTCTGAGTTTCTAATGTAGTC | (SEQ. ID. NO: 7) |
| ΔK2 huHGF: | CATAGTATTGTCAGCTTCAACTTCTGAACA | (SEQ. ID. NO: 8) |
| ΔK3 huHGF: | TCCATGTGACATATCTTCAGTTGTTTCCAA | (SEQ. ID. NO: 9) |
| ΔK4 huHGF: | TGTGGTATCACCTTCATCTTGTCCATGTGA | (SEQ. ID. NO: 10) |
| N-303 huHGF: | ACCTTGGATGCATTAAGTTGTTTC | (SEQ. ID. NO: 11) |
| N-384 huHGF: | TTGTCCATGTGATTAATCACAGT | (SEQ. ID. NO: 12) |
| α-chain: | GTTCGTGTTGGGATCCCATTTACCTATCGCAATTG | (SEQ. ID. NO: 13) |

The Y673S, V692S huHGF variant was obtained from wild-type huHGF as a template, using both oligonucleotides used for generating the two mutations.

The mutant huHGF constructs generated using the protocol above were transformed in *E. coli* host strain MM294tonA using the standard calcium chloride procedure (Sambrook et al., supra) for preparation and transformation of competent cells. MM294tonA (which is resistant to T1 phage) was prepared by the insertion and subsequent imprecise excision of a Tn10 transposon into the tonA gene. This gene was then inserted, using transposon insertion mutagenesis [Kleckner et al., *J. Mol. Biol.* 116, 125–159 (1977)], into *E. coli* host MM294 (ATCC 31,446).

The DNA extract from individual colonies of bacterial transformants using the standard miniprep procedure of Sambrook et al., supra. The plasmids were further purified by passage over a Sephacryl CL6B spin column, and then analyzed by sequencing and by restriction endonuclease digestion and agarose gel electrophoresis.

B. Transfection of Human Embryonic Kidney 293 Cells

Plasmids with the correct sequence were used to transfect human fetal kidney 293 cells by the calcium phosphate method. 293 cells were growth to 70% confluence in 6-well plates. 2.5 μg of huHGF plasmid DNA variant was dissolved in 150 μl of 1 mM Tris-HCl, 0.1 mM EDTA, 0.227M $CaCl_2$. Added to this (dropwise while vortexing) was 150 μl of 50 mM HEPES buffer (pH 7.35), 280 mM NaCl, 1.5 mM $NaPO_4$, and the precipitate was allowed to form for ten minutes at 25 °C. The suspended precipitate was then added to the cells in the individual wells in a 6-well plate. The cell monolayers were incubated for 4 hours in the presence of the DNA precipitate, washed once with PBS, and cultured in serum-free medium for 72 h. When stable populations were made, the HGF cDNA was subcloned in an episomal CMV driven expression plasmid pCisEBON (G. Cachianes, C, Ho, R. Weber, S. Williams, D. Goeddel, and D. Lueng, in preparation). pCisEBON is a pRK5 derivative that includes sequences encoding a selectable marker gene encoding neomycin phosphotransferase (NEO), an origin of replication derived from Epstein Barr virus origin (ori P) and the viral EBNA-1 gene. The product of the EBNA-1 gene promotes stable, episomal replication of plasmids containing the ori P sequence [see Cachianes, G. et al., *Technique*, in press (1992)]. The nucleotide sequence encoding pCisEBON is disclosed in copending application Ser. No. 07/885,971 filed 18 May, 1992. The populations were directly selected in Neomycin selective medium.

EXAMPLE 2

Assay Methods

In view of the pleiotropic activities of HGF, a molecule with a structure unlike any other known growth factor, it is important to understand the molecular interaction of this factor with its receptor. The huHGF variants produced as described in Example 1 were analyzed for their ability to induce DNA synthesis of hepatocytes in primary culture and to compete for binding to a soluble form of the huHGF receptor.

A. Protein quantification of wild-type huHGF and huHGF variants

A specific two-site huHGF sandwich ELISA using two monoclonal antibodies was used to quantify wild-type recombinant huHGF (WT rhuHGF), single chain and protease substitution variants. Microtiter plates (Maxisorb, Nunc) were coated with 10 mg/ml of a monoclonal anti-rhuHGF antibody A 3.1.2 (IgG2a phenotype, affinity: 3.2× $10^{-8}$ mol) in 50 mM Carbonate buffer, pH 9.6, overnight at 4° C. After blocking plates with 0.5% BSA (Sigma), 0.01% thimerosal in PBS, pH 7.4, and subsequent washes, duplicate serial dilutions of HGF samples were prepared and in parallel a CHO-expressed rhuHGF (40-0.1 ng/mL) was used as a standard. Fifty microliters of these dilutions were simultaneously incubated with 50 mL of a 1:1500 diluted horseradish peroxidase conjugated monoclonal anti-rhuHGF antibody B 4.3 (IgG1 phenotype, affinity: $1.3 \times 10^{-x}$ mol) for 2 h at RT. The substrate was prepared by adding 0.04% o-phenylenediamine-dihydrochloride (Sigma) and 0.012% (v/v) hydrogen-peroxide (Sigma) to PBS and 100 ml were added to the washed plates for 15 minutes at RT. The reaction was stopped by adding 50 mL of 2.25M sulfuric acid to each well. The absorbance at 490 nm, with the absorbance at 405 nm subtracted as background, was determined on a microtiter plate reader (Vmax, Molecular Devices, Menlo Park, Calif.). The data was reduced using a four-parameter curve-fitting program developed at Genentech, Inc.

An HGF polyclonal sandwich ELISA was used to quantify all kringle deletion and C-terminal truncation variants. Briefly, microtiter plates (Nunc) were coated with 5 mg/mL guinea pig polyclonal (anti CHO-expressed rhuHGF) IgG antibody preparation (Genentech, Inc.) as described above. This antibody recognizes rhuHGF as well as HGF truncated forms when compared to visual inspection of Western blots, making it ideal for monitoring HGF variants. Plates were blocked and duplicate serial dilutions of 293 cell supernatants (1:103-6.106) were added and incubated over night at 4° C. Purified CHO-expressed rhuHGF (100-0.78 ng/mL) was used as a standard and incubated in parallel. Plates were washed and incubated with a 1:500 dilution of the same polyclonal antibody (approx. 400 ng/mL) but in this case horseradish peroxidase conjugated for detection of the variants (see above). Western blotting was performed to determine the size of the expressed HGF variants. For this, SDS-polyacrylamide gel electrophoresis and Western blotting were performed using standard methods with the polyclonal IgG antibody preparation (500 ng/mL). A chemiluminescent detection method (Amersham) and a goat anti-guinea pig IgG-horseradish peroxidase conjugate (1:5000) were used for development of the blot as described by the manufacturer.

B. Soluble HGF receptor binding assay

Previous studies on HGF binding to hepatocytes have shown that huHGF could bind to its cell surface receptor with high affinity (Kd~24–32 pM; Higuchi and Nakamura, *Biochem. Biophys. Res. Comm.* 174, 831–838 (1991)). We preferred to examine HGF binding using a soluble form of the receptor because of the nonspecific binding of HGF to cell surface heparin sulfate proteoglycans [Naldini et al., *EMBO J.* 10, 2867–2878 (1991)].

Cell supernatants (concentrated on Amicon filters if concentration was below 600 ng/mL) were tested for their ability to block in solution the binding of CHO-expressed $^{125}I$ rhuHGF (2–5×103 Ci/mmole, kindly provided by T. Zioncheck, Genentech, Inc.) to the extracellular domain of the human HGF receptor (huHGFr) fused to the Fc constant region of an human IgG, expressed and secreted from 293 cells.

1. Construction of huHGFr-IgG chimeras

A full length cDNA clone encoding the huHGFr was constructed by joining partial cDNAs isolated from cDNA libraries and from PCR amplification. Coding sequences for amino acids 1–270 were isolated from a human placental CDNA library (provided by T. Mason, Genentech) screened with a 50 mer oligonucleotide (5'-ATGAAGGCCCCCGCTGTGCTTGCACCTGGCATC-CTCGTGCTCCTGTTTACC-3') (SEQ. ID. NO: 15). Sequences encoding amino acids 809–1390 were isolated from a human liver library (Stragagen) screened with the oligonucleotide probe (5'-CACTAGTTAGGATGGGGGACATGTCTGT-CAGAGGATACTGCACTTGTCGGCATGAA CCGT-3'). (SEQ. ID. NO: 16)

Conditions for plating libraries, and for hybridization and washing filters were as described [Godowski et al., *Proc. Natl. Acad. Sci. USA* 86, 8083–8087 (1989)]. PCR was used to isolate a cDNA clone containing residues 271–808 of the HGFr (c-met) from A549 cells. Ten $\mu$gs of total RNA was used for reverse transcription using a primer specific to the HGFr (5'-TAGTACTAGCACTATGATGTCT -3') (SEQ. ID. NO: 17) in a 100 $\mu$l reaction using Moloney murine leukemia virus reverse transcriptase and buffers supplied by Bethesda Research Laboratories. One-tenth of this reaction mixture was used for PCR amplification. The PCR reaction was performed in a volume of 100 $\mu$l containing 10 $\mu$l of the reverse transcriptase reaction, 10 mM KCl, 20 mM Tris-HCl (pH 8.8), 10 mM (NH4)SO4, 6 mM MgSO4, 0.1% Trition X-100, 1 U of Vent DNA polymerase (New England Biolabs) and 50 pmol each of the forward primer (5'-TTTACTTCTTGACGGTCCAAAG-3' (SEQ. ID. NO: 18) and the reverse primer (5'-CAGGGGGAGTTGCAGATTCAGCTGT-3') (SEQ. ID. NO: 19). After thirty cycles of denaturation (95° C., 1 min), annealing (55° C., 45 secs) and extension (72° C., 2 min), the PCR product were recovered from low-melting temperature agarose gels. The full-length HGFr cDNA was subcloned into vector pRK7 (see Wo 90/02798, published 22 Mar., 1990) and double-stranded DNA sequencing was performed by the dideoxynucleotide method.

The coding sequence of the extracellular domain of the huHGFr was fused to those of the human IgG1 heavy chain in a two-step process. PCR was used to generate a fragment with a unique BstEII site 3' to the coding sequences of the HGFr amino acid 929. The 5' primer (located in the vector upstream of the HGFr coding sequences) and the 3' primer (5'-AGTTTTGTCGGTGACCTGATCATTCTGATCTGGT-TGAACTATTAC-3') (SEQ. ID. NO: 20) were used in a 100 pl reaction as described above except that the extension time at 72° C. was 3 minutes, and 40 ng of the full length HGFr expression vector was used as template. Following amplification, the PCR product was joined to the human IgG-γ1 heavy chain cDNA through a unique BstEII site in that construct [Bennett et al., *J. Biol. Chem.* 266, 23060–23067 (1991)]. The resulting construct contained the coding sequences of amino acids 1–929 of the huHGFr fused via the BstEII site (adding the coding sequences for amino acids V and T) to the coding sequences of amino acids 216–443 of the human IgG-γ1 heavy chain. Sequencing of the construct was carried out as described above.

2. Binding assay

The binding assay was performed in breakable microtiter plates (Nunc) coated o/n at 4° C. with 1 mg/mL of rabbit-anti-human IgG Fc specific antibody (Jackson Immunoresearch) and plates were carefully washed with PBS containing 0.05% Tween 20 (Biorad). After blocking with PBS containing 0.1% BSA, in this same buffer, 50 pM of 125I-rhuHGF in 25 mL per well were added. To each well 50 mL of serial dilutions (1:25–1:6000) of cell supernatants, purified CHO-expressed rhuHGF (25,000-0.064 pM) or medium were added in duplicates. Subsequently, 25 mL of 50 pM of HGF receptor:IgG fusion protein were added and the plates were incubated with gentle shaking. After 4 hours, when equilibrium was reached, plates were washed and wells were individually counted in a gamma-counter. The amount of nonspecifically bound radioactivity was estimated by incubating HGF receptor:IgG with a 500-fold excess of unlabelled rhuHGF. The dissociation constant (Kd) of each analogue was calculated at the IC50 from fitted inhibition curves using the huHGF concentration determined by ELISA.

C. Biological assay

The biological activity of WT huHGF and variants was measured by their abilities to induce DNA synthesis of rat hepatocytes in primary culture. Hepatocytes were isolated according to published perfusion techniques with minor modifications [Garrison and Haynes, *J. Biol. Chem.* 150, 2269–277 (1975)]. Briefly, the livers of female Sprague Dawley rats (160–180 g) were perfused through the portal vein with 100 mL of $Ca^{++}$ free Hepes buffered saline containing 0.02% Collagenase type IV (Sigma). After 20 minutes the liver was removed, placed in buffer, gently stirred to separate hepatocytes from connective tissue and blood vessels, and filtered through nylon mesh. Cells were then washed by centrifugation, resuspended at $1 \times 10^5$ cells/mL in Williams Media E (Gibco) containing Penicillin (100 U/ml), Streptomycin (100 mg/mL), L-Glutamine (2 mM), trace elements (0.01%), transferrin (10 mg/mL) and Aprotinin (1 mg/mL). Hepatocytes were incubated in 96-well microtiter plates (Falcon) in the presence of duplicate serial dilutions of either purified CHO-expressed rhuHGF (1-0.031 mg/mL), 293 supernatants (1:4–1:256) or medium. After 48 hours incubation at 37° C., 0.5 mCi 3 H-TdR (15 Ci/mmole, Amersham) was added to each well and incubated for an additional 16 hours. Cells were harvested on filter papers, which were washed, dried and counted in a Beckman counter after addition of scintillation liquid. For each huHGF variant, the specific activity (SA) expressed in units/mg was calculated at half-maximal proliferation (defined as 1 unit/mL) using the HGF concentration obtained in ELISA.

D. Induction of tyrosine phosphorylations on A549 cells

Human lung carcinoma cells (A549) monolayers were cultured in RPMI 1640 medium containing 10% fetal bovine serum and maintained at 37° C. in a humidified atmosphere with 5% $CO_2$. Serum-starved cells were incubated without or with 200 ng/mL rhuHGF for 5 minutes at 37° C. and extracted with lysis buffer containing 50 mM Hepes, 150 mM NaCl, 1.5 mM $MgCl_2$, 1 mM EGTA, 10% Glycerol, 1% Triton X-100 and a cocktail of protease inhibitors. The lysates were immunoprecipitated with anti-Met COOH antibodies and blotted with anti-phosphotyrosine antibodies (see Western blotting above).

EXAMPLE 3

Analysis of Cleavage Site Mutants

Figure 2:
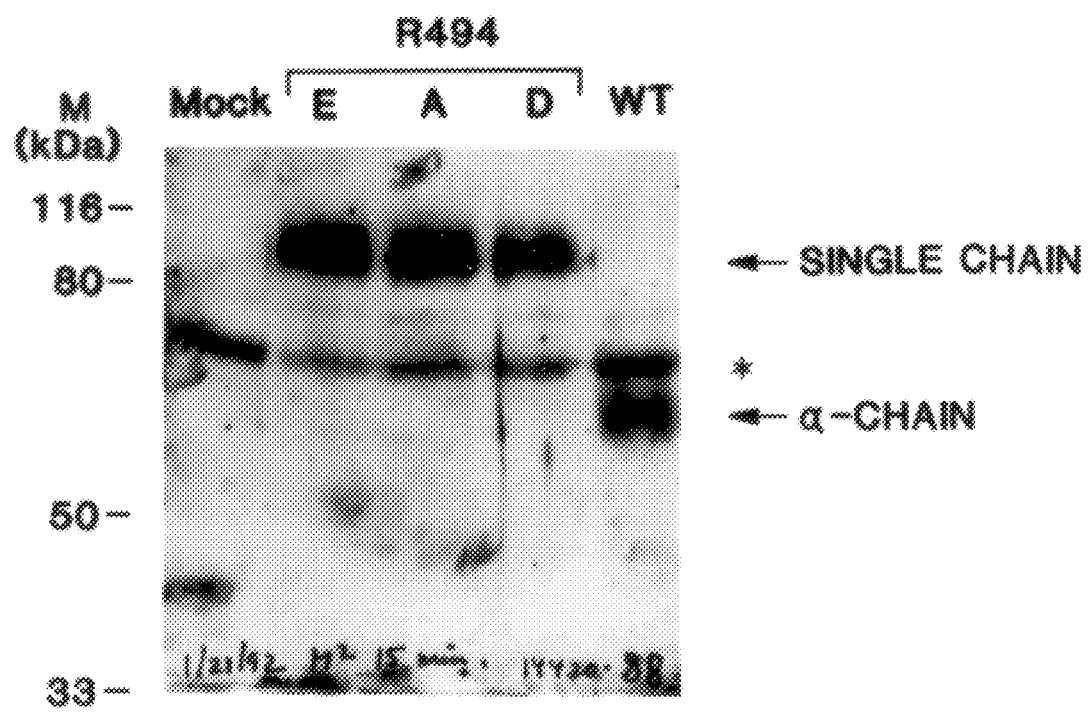
FIG. 2 shows the results of Western blot of wild-type rhuHGF and single-chain variants. Conditioned media from mock transfected 293 cells or stable 293 cells expressing either wild-type rhuHGF (WT) or the variants R494E, R494A or R494D were fractionated under reducing conditions on an 8% sodium-dodecyl sulfate-polyacrylamide gel and blotted. The blot was reacted with polyclonal anti-HGF antisera which recognizes epitopes primarily in the α-chain. Molecular masses (kilodaltons) of the marker are as indicated. Also indicated are the positions of the α-chain and uncleaved single-chain forms of huHGF. Note that the polyclonal antibody cross-reacts with an unidentified band (*) present even in the control transfected 293 cells, which do not express detectable quantities of huHGF.
Figure 3A:
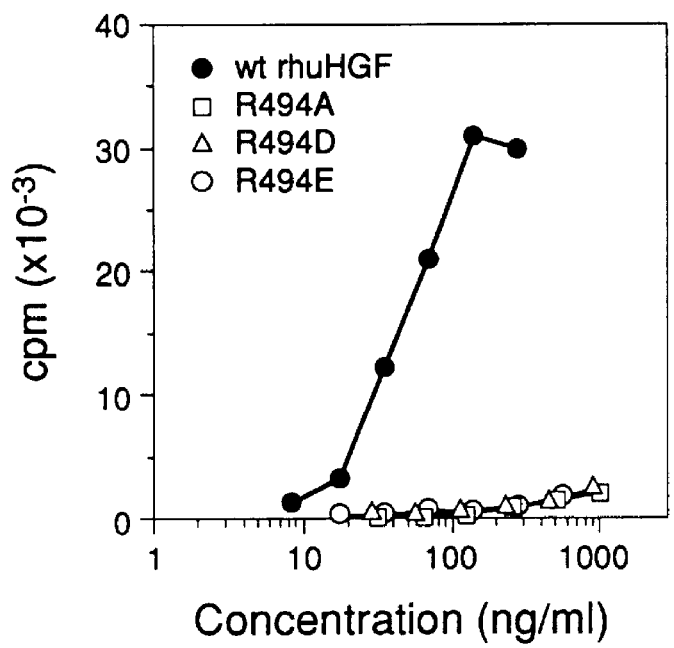
FIGS. 3A–B: Mitogenic activity (A) and competitive receptor binding (B) of wild-type (WT) rhuHGF and single-chain variants. (A) Biological activity was determined by the ability of WT rhuHGF and variants to induce DNA synthesis of rat hepatocytes in primary culture as described in Example 2. Shown are the mean cpm from duplicates in a representative assay. Mock supernatant from control cells did not stimulate DNA synthesis in these cells (no cpm increase above background levels). (B) To perform competitive binding, various dilutions of supernatants of human 293 cells containing wt rhuHGF or variants were incubated with 50 pM of the huHGF receptor-IgG fusion protein as described in Example 2. Data represent inhibition of binding as the percentage of any competing ligand from a representative experiment and were corrected by subtraction of background values from control 293 cells.
Figure 3B:
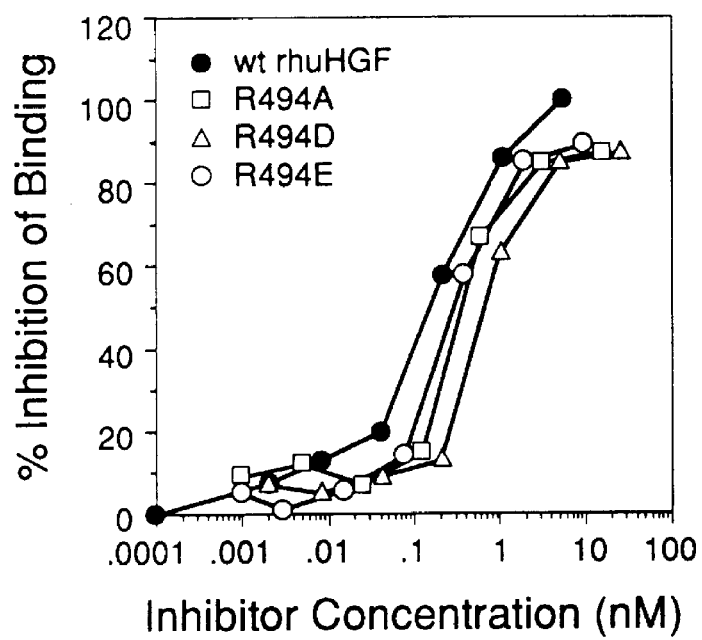

The cleavage site of proteases commonly contains a basic residue at position P1 and two hydrophobic amino acid resides in positions P'1 and P'2, which follow the cleaved peptide bond. The proposed cleavage site of huHGF (P1 R494, P'1 V495, P'2 V496) fits this consensus. We chose to try to block cleavage of huHGF by replacing the P1 R494 with either D, E, or A. The major form of WT rhuHGF expressed in these cells is cleaved into two-chain material as judged by the presence of the α-chain with an apparent molecular mass of 69 kDa (FIG. 2). Each of these mutations appeared to block processing of rhuHGF because under reducing conditions these variants migrated as a single band at 94 kDa, the predicted size of single-chain HGF. These variants totally lacked the ability to induce the proliferation of hepatocytes in primary culture (FIG. 3A). However, when these variants were analyzed for their ability to compete with WT rhuHGF for binding to the HGF receptor:IgG fusion protein, their inhibition curves were roughly similar to that of WT rhuHGF (FIG. 3B). The Kd determined from these curves showed that WT rhuHGF binds to the fusion protein with high affinity (50–70 pM) whereas all single chain variants showed approximately a 2- to 10-fold higher Kd (100–500 pM) compared to WT rhuHGF. Results from at least three independent assays are summarized in Table I as residual hepatocyte proliferative activity and receptor binding capacity compared to WT rhuHGF.

Our binding studies showed that WT rhuHGF bound to the soluble receptor fusion protein with a single class of high affinity binding sites (50–70 pM), similar to those found on hepatocytes by Higushi and Nakamura (1991). However, binding of HGF on cells may slightly be different since the soluble receptor is actually a dimer held together by the disulfide bridge of the hinge in the Fc portion of the IgGA.

Direct comparison of specific activity (SA) versus Kd ratios of all single chain variants showed they were inactive at the highest concentration tested (SA<3%) while receptor binding affinities were only decreased by a factor of 2–3.

These results argue strongly that cleavage of HGF into the two-chain form is required for mitogenic activity, i.e. that single-chain HGF is a promitogen and that the uncleaved form of HGF binds to the HGF receptor, albeit with a reduced affinity.

The major form of HGF isolated from placenta [Hernandez et al., (1992) J. Cell Physiol., in press] or expressed in transfected COS cells [Rubin et al., Proc. Natl. Acad. Sci. USA 88, 415–419 (1991)] is in single-chain form. When tested in mitogenic assays, this single-chain form of HGF is found to be biologically active. Taken together with our data, this suggests that this single-chain HGF is activated to the two-chain form during the mitogenic assay.

A second observation is that single-chain HGF variants retain substantial capacity to bind to the HGF receptor, as suggested by our competition binding assays. This raises the interesting possibility that single-chain HGF may be bound to cell-surface HGF receptor in vivo in an inactive state and can subsequently be cleaved to the active double-chain form by the appropriate protease.

EXAMPLE 4

The Effects of Protease Domain Mutations

To elucidate the functional importance of the protease domain of HGF, several single, double and triple mutations were made in order to reconstitute a potential serine-protease active site. The construction of these variants is described in Example 1.

We replaced HGF residues Q534 with H, Y673 with S, or V692 with S as either single, double or triple mutations. The analysis of their effects on mitogenic activity and receptor binding showed that the single mutation Q534H did not significantly alter either SA (5.2×104 Units/mg) or Kd (60 pM) when compared to wt rhuHGF (respectively 3.3 104 Units/mg and 70 pM) whereas Y673S and V692S exhibited SA reduced approximately 5-and 10-fold, respectively. In fact, these two variants never reached the maximum plateau seen with WT rhuHGF (approximately 50% of wt rhuHGF plateau). Interestingly, these variants showed a Kd similar to WT rhuHGF. All other double and triple variants also retained the ability to bind the HGF receptor but they clearly showed a reduced SA (Table I). The residual SA of the double variants Q534H,Y673S and Y673S,V692S and of the triple variant Q534H,Y673S,V692S were less than 3% compared to WT rhuHGF. However, the Kd of these variants was not significantly different from WT rhuHGF (Table I). These variants indicate that mutations within the β-chain of HGF block mitogenic activity but they are still able to bind to the HGF receptor. Thus, it appears that these mutants are defective in an activity subsequent to receptor binding.

These results show that although the β-chain is not required for receptor binding, certain residues (e.g. Y673 and V692) are critical for the structure and/or activity of HGF. Substitution of the nonpolar residue V692 with the polar residue S might have caused a structural transition if new hydrogen bonds to the active site residue D594, as found in serine-proteases, have been introduced. Substitution of Y673 with the smaller residue S might also introduce some local structural modifications. On the other hand, replacement of the polar residue Q534 by another polar residue H of similar size would not likely cause a drastic difference in the HGF conformation as this residue should be exposed; indeed the Q534H variant was similar to rhuHGF (Table I).

EXAMPLE 5

The Effect of C-terminal and Kringle Deletions

In order to ascertain whether the α-chain is required for HGF binding or activity, C-terminal truncations were made as described in Example 1, resulting in variants containing either the α-chain alone, or variants truncated after the third (N-384) or second (N-303) Kringles.

A number of C-terminal truncations of HGF were made by deleting either the β-chain or the β-chain in addition to a progressive number of kringles as depicted in FIG. 1. One variant (N-207) corresponding to the N-terminal domain with the first Kringle did not express the protein to levels detectable either by Western blotting or ELISA using a polyclonal antibody preparation and thus was not investigated further. Expression of the variants containing the first two Kringles (N-303), three Kringles (N-384) or the complete α-chain of HGF was as low as 250–600 ng/mL. A summary of the residual SA and Kd compared to WT rhuHGF of these variants is presented in Table I. At the concentration tested no activity above background levels was observed indicating that these variants lost their biological activity. However, binding competition showed that variants N-303, N-384 or the α-chain still retained substantial binding capacity (up to 23% compared to WT rhuHGF binding). Thus, the N-terminal 272 residues of HGF (the mature form of variant N-303) are sufficient for high affinity binding to the HGF receptor. Results from deleting each kringle domain are shown in Table I. Deletion of the first Kringle (variant ΔK1) of HGF affected biological activity most, showing at least a 100-fold reduction (SA<0.2% of wt rhuHGF). Similarly, binding of this variant was also affected as it failed to compete for binding with wt rhuHGF up to 2 mg/mL. Deletion of all other Kringles (variants ΔK2, ΔK3 or ΔK4) also induces severely reduced mitogenic activity (Table I). However, the Kds of these deletion variants remained close to that observed with wt rhuHGF.

These data show that Kringles K3 and K4 are not required for receptor binding. Our data support the previous observations by Miyazawa et al., 1991 supra and Chan et al., 1991 supra, in the sense that variant N-303, which in amino acid sequence is very similar to HGF/NK2, retains the ability to compete efficiently for binding to the HGF receptor (Kd~280 pM). Furthermore, the observations that N-303 is sufficient to bind to the receptor and that the second Kringle is not required for binding the HGF receptor (in the context of the remainder of the molecule) suggest that the receptor binding domain is contained within the finger and first Kringle of huHGF. Unfortunately, we have not been able to detect expression of this variant using our polyclonal antisera suggesting that variant N-207 (deletion after the first kringle) was not expressed in 293 cells.

TABLE I

| Variants (var) | SA var/SA wt +/- S.D. | Kdwt/Kdvar +/- S.D. |
|---|---|---|
| Single-chain | | |
| R494A | <0.03 | 0.32 +/- 0.18 |
| R494D | <0.03 | 0.51 +/- 0.21 |
| R494E | <0.02 | 0.31 +/- 0.13 |
| Protease | | |
| Q534H | 1.19 +/- 0.44 | 1.48 +/- 0.85 |
| Y673S | 0.27 +/- 0.07* | 1.35 +/- 0.72 |
| V692S | 0.08 +/- 0.04 | 1.02 +/- 0.13 |
| Q534H, Y673S | <0.03 | 2.24 +/- 1.11 |
| Y673S, V692S | <0.02 | 1.76 +/- 0.63 |
| Q534H, Y673S, V692S | <0.02 | 1.91 +/- 1.28 |
| C-terminal truncation | | |
| N-303 | <0.05 | 0.23 +/- 0.03 |
| N-384 | <0.05 | 0.25 +/- 0.02 |
| α-chain | <0.04 | 0.25 +/- 0.03 |
| Kringle deletion | | |
| ΔK1 | <0.002 | <0.03 |
| ΔK2 | <0.05 | 0.41 +/- 0.18 |
| ΔK3 | <0.03 | 0.56 +/- 0.36 |
| ΔK4 | <0.07 | 0.86 +/- 0.46 |

EXAMPLE 6

Induction of Tyrosine-Phosphorylation of the huHGF Receptor

Figure 4:
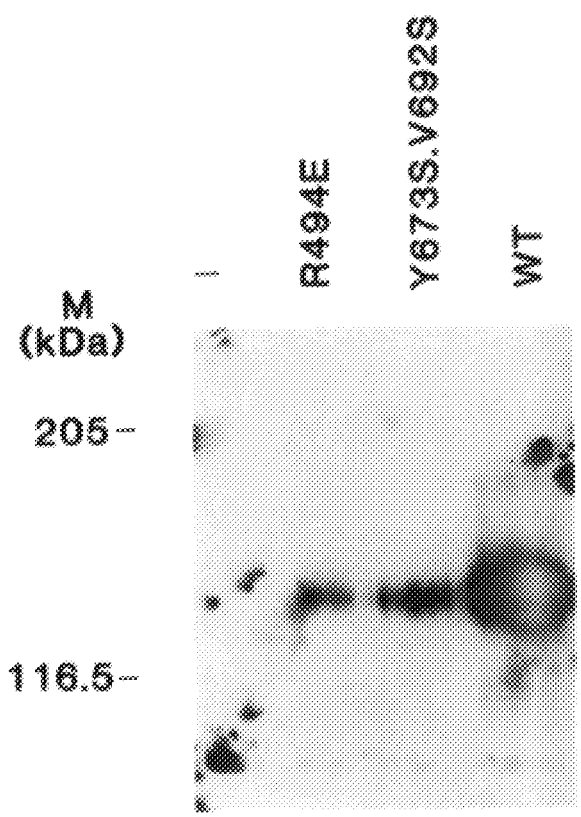
FIG. 4: Western blot of ligand-induced tyrosine-phosphorylation on the 145 kDa β-subunit of the HGF receptor by wild-type rhuHGF, single-chain or protease domain huHGF variants. Lysates from A549 cells incubated for 5 minutes without (−) or with 200 ng/mL of purified wt rhuHGF (WT), single-chain (R494E) or double protease variants (Y673S,V692S) were prepared and immunoprecipitated with an anti-HGF receptor antibody and blotted with anti-phosphotyrosine antibodies. Molecular masses (kilodaltons) are as indicated.

We determined if variants R494E or Y673S,V692S, which bind the HGF receptor in vitro but are defective for mitogenic activity, could stimulate tyrosine-phosphorylation of the HGF receptor in A549 cells. Serum starved cells were treated with purified WT rhuHGF or variants and immunoprecipitates of the HGF receptor were blotted and probed with phosphotyrosine antibodies. Stimulation with wt rhu-HCF led to the phosphorylation on tyrosine of the 145 kDa β-subunit of the HGF receptor (FIG. 4). Both variants exhibited a reduced ability to induce phosphorylation of the HGF receptor.

Stimulation of tyrosine phosphorylation on the HGF receptor β-subunit by HGF was previously reported [Bottaro et al., Science 251, 802–804 (1991), Naldini et al., 1991 supra]. The present data show that variants R494E and Y673S,V692S can bind the soluble HGF receptor: IgG protein in vitro but are not efficient in stimulating tyrosine-phosphorylation in A549 cells. One interpretation of this result is that these variants are capable of binding the HGF receptor on A549 cells, but are defective in a function required to induce efficient phosphorylation, e.g. receptor dimerization. It has been shown for other receptor proteins with an intrinsic tyrosine kinase such as the epithelial and platelet-derived growth factor that receptor-receptor interactions or dimerization is required for activation of kinase function [see for review Ulrich and Schlessinger, Cell 61 203–212 (1990)]. Alternatively, these variants may not be able to bind the cell-surface associated HGF receptor.

The unique structure of HGF suggests that there may be multiple events that regulate the biological activity of this molecule. An early stage of regulation may be the cleavage step to generate the biologically active two-chain form. Interestingly, cleavage may not simply regulate receptor binding but rather control a subsequent event required for activating the HGF receptor. Our data also suggest that the β-chain, while not absolutely required for receptor binding contributes to a receptor activation step. These variants may be useful in dissecting the signalling events at the HGF receptor.

EXAMPLE 7

Construction and Expression of HGF-IQG Chimeras

The unique Kpn I site in the coding sequence of wild-type huHGF was linked to the unique BstE II site of a human IgG-γ1 heavy chain cDNA by a double-stranded synthetic linker [5'-CACAGTCG-3' (SEQ. ID. NO: 21) and 5'-GTGACCGACTGTGGTAC-3' (SEQ. ID. NO: 22)]. The resulting construct contained the coding sequences for the entire 728 amino acids of HGF fused by two amino acids (V and T) to amino acids 216–443 of the IgG-γ1 heavy chain.

The coding sequences of the HGF variants R494E, and Y673S,V692S (prepared as described in Example 1) were fused in an identical fashion to IgG-γ1.

To construct NK2 HGF-IgG (for brevity also referred to as NK2-IgG), a double stranded synthetic linker 5'-ACTGTGCAATTAAAACATGCGAGACG-3' (SEQ. ID. NO: 23) 5'-GTGACCGTCTCGCATGTTTTAATTGCACAGT-3' (SEQ. ID. NO: 24) was used to join the unique Sca I site in IHG to the BstE II site of the IgG-β1 heavy chain cDNA construct described above. This reconstitutes the coding sequence of the naturally occurring HGF/NK2 variant described by Miyazawa et al., supra.

NK1 HGF-IgG (also referred to as NK1-IgG) was constructed by "loop out" deletion mutagenesis using a single-stranded HGF-NK2 template. The mutagenic oligonucleotide used was 5'-GTCGGTGACCGTCTCTTCAACTTCTGAACA-3' (SEQ. ID. NO: 25). The resulting cDNA contained the coding sequences for amino acids 1–210 of HGF joined to those encoding amino acids 216–443 of IgG-γ1 via linker sequences encoding amino acids E, T, V and T.

Expression in 293 cells was performed as hereinabove described.

Figure 5A:
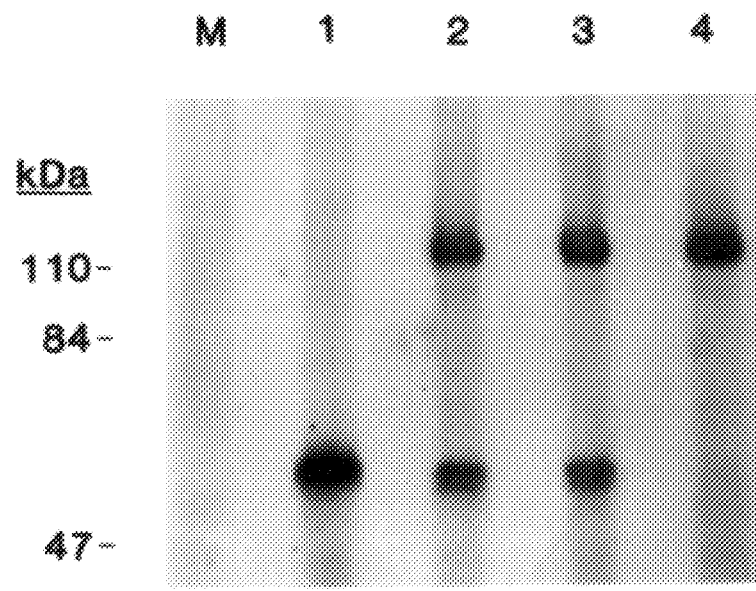
FIGS. 5A–C: Expression and proposed structures of HGF-IgG chimeras. A. SDS-PAGE gel electrophoresis under reducing conditions. B. SDS-PAGE gel electrophoresis under non-reducing conditions. Lane M: control (Mock) 293 cells; Lane 1: NK2-IgG; Lane 2: HGF-IgG; Lane 3: Y673S,V692S-IgG; Lane 4: R494E HGF-IgG. C. Proposed structures of HGF variant-IgG chimeras.
Figure 5B:
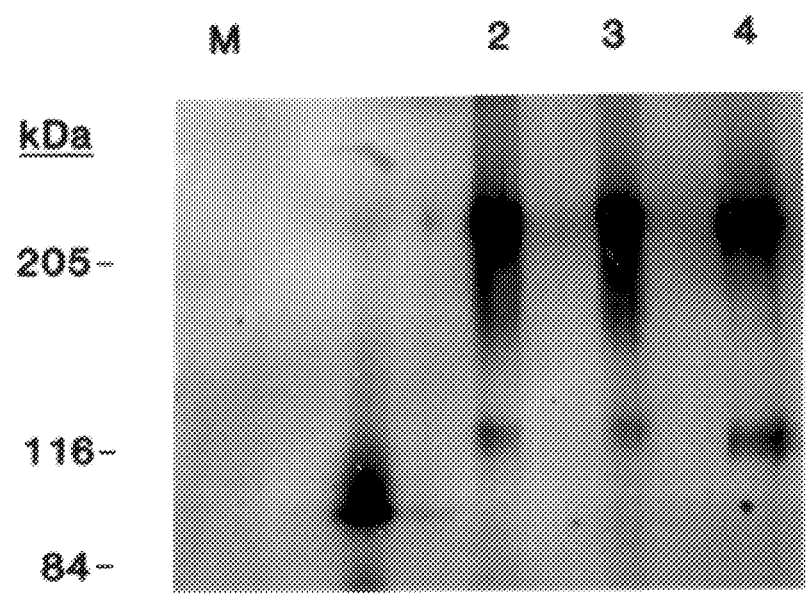

Control 293 cells and those expressing the HGF-IgG chimeras were analyzed by electrophoresis on an 8% SDS-PAGE under reducing (FIG. 5A) and non-reducing (FIG. 5B) conditions. Lane M (Mock) shows that no expression was detected in control cells. The other lanes represent the following chimeras:

Lane 1: N-303-IgG

Lane 2: HGF-IgG

Lane 3: Y673S,V692S HGF-IgG

Lane 4: R494E HGF-IgG

The results of SDS-PAGE electrophoresis clearly indicate that the chimeras were expressed as dimers.

Figure 5C:
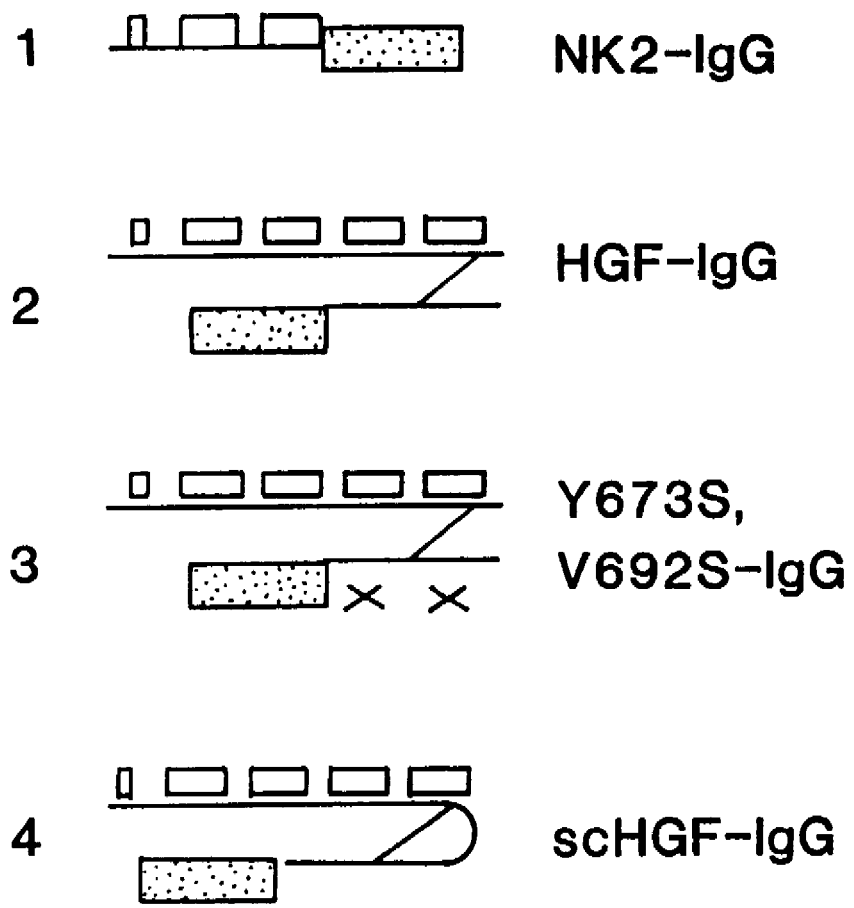

The proposed structures for these HGF-variant-immunoglobulin chimeras are shown in FIG. 5C.

EXAMPLE 8

Binding of HGF-IaG Chimeras to Endogenous HGFr in A549 Cells

The ability of either wild-type recombinant human HGF (wt rhuHGF) or HGF variant-IgG chimeras to compete for binding of $^{25}$I-labeled rhuHGF to A549 cells was studied essentially as described by Naldini, L. et al., *EMBO J.* 10, 2867–2878 (1991) with minor modifications. A549 cells, seeded in 24 well plates at a density of $10^4$ cells/well, were grown overnight in DMEM [?] and then shifted to serum free media for 2 hours. Binding was performed with gentle shaking at 4° C. for 3 hours in Hanks media containing 20 mM HEPES, 0.2% BSA and 0.02% $NaN_3$, pH 7.0. Each well received 50 pM $^{125}$I-rhuHGF or HGF variant and the indicated concentrations of competitor. Extractions and washes were performed as described in Naldini et al., supra.

Figure 6:
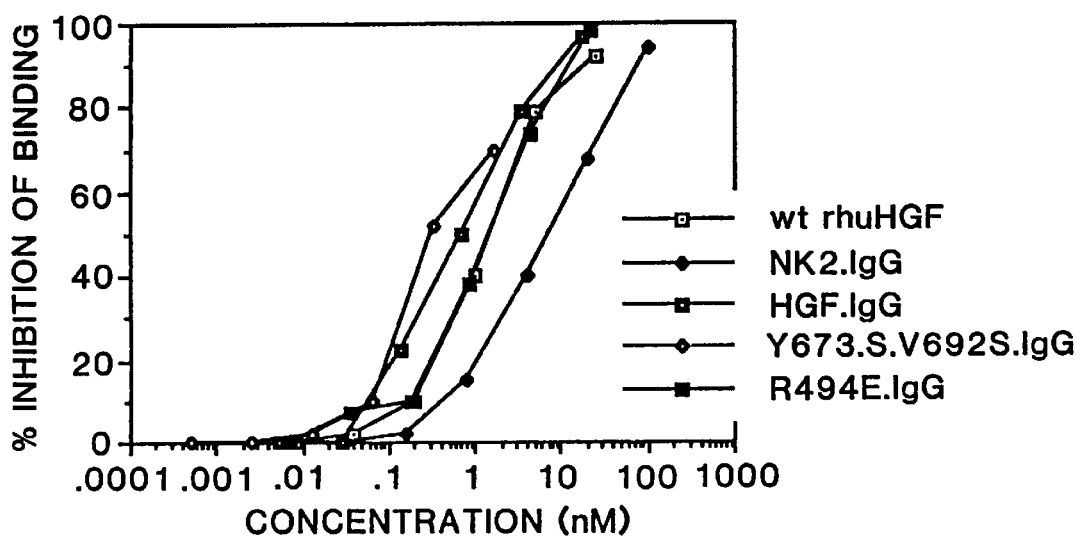
FIG. 6: Competitive binding assay. Cell culture supernatants of 293 cells expressing wild-type rhuHGF and various huHGF variant-IgG chimeras were tested for their ability to block the binding of CHO cell expressed $^{125}$I rhuHGF to the extracellular domain of the human HGFr fused to the Fc constant region of human IgG-1, expressed and secreted from 293 cells.

The results shown in FIG. 6 demonstrate that the HGF-IgG chimeras bind to endogenous HGFr in A549 cells similar to wild-type human HGF (wt rhuHGF).

EXAMPLE 9

Mitogenic Effect on Primary Rat Hepatocyte Cultures

The variant HGF molecules and the HGF variant-IgG chimeras were quantified in the two-site huHGF sandwich ELISA assay described in Example 2A. Conditioned media from 293 cells expressing wt rhuHGF, the indicated HGF variants, and HGF variant-IgG chimeras were tested for mitogenic effect on primary rat hepatocyte cultures in the 4H-thymidine uptake assay described in Example 2C. The results are shown in FIGS. 7A, 7B and 7C.

Figure 7A:
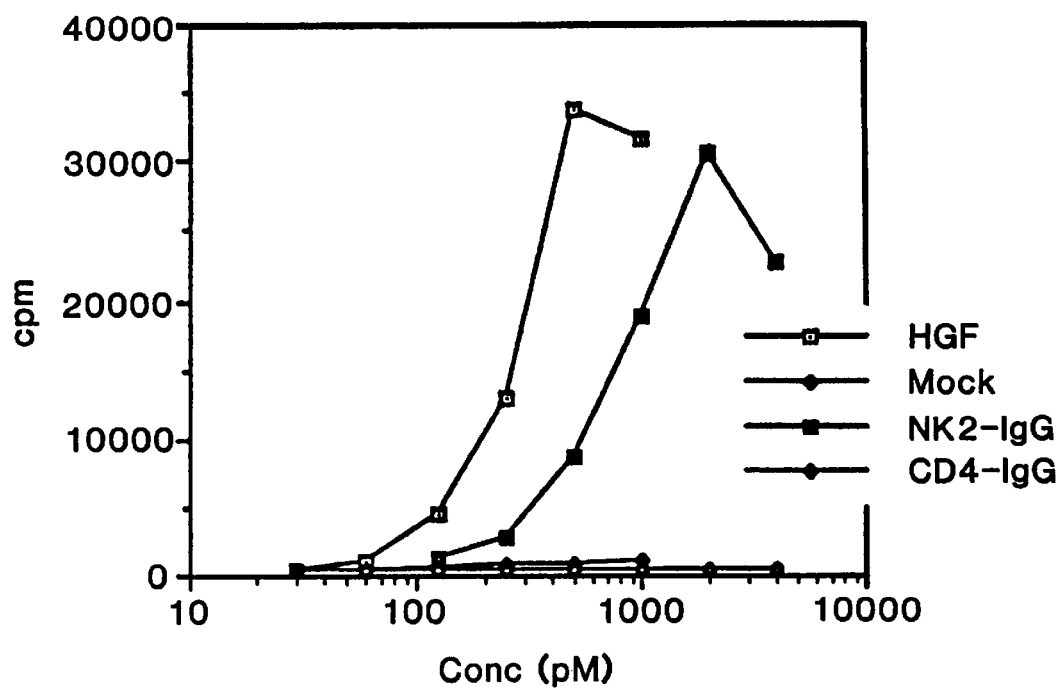
FIGS. 7A–C: 3H-thymidine uptake assay. Conditioned media from 293 cells expressing wild-type rhuHGF and various rhuHGF variant-IgG chimeras were tested for mitogenic effect in a 3H-thymidine uptake assay. Mock: control 293 cells.
Figure 7B:
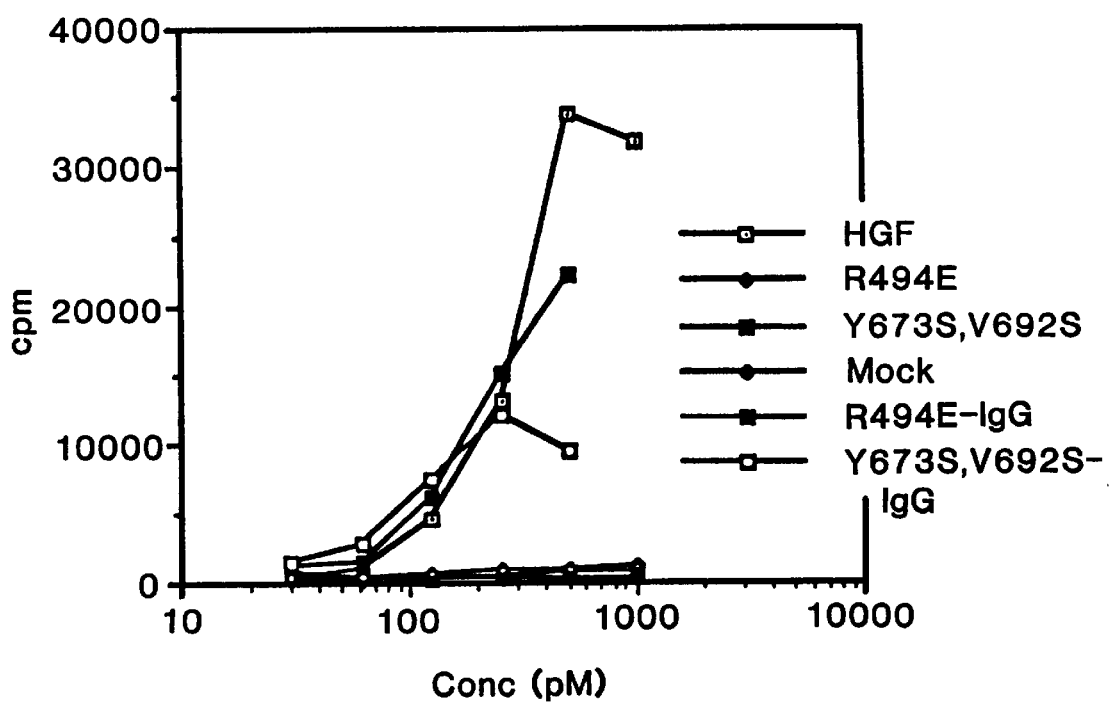
Figure 7C:
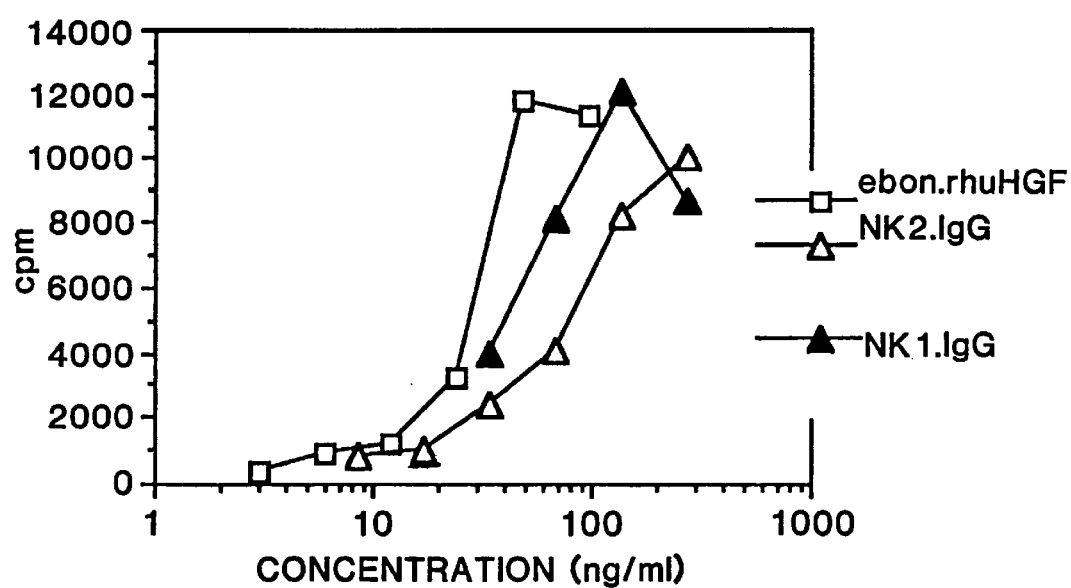

As demonstrated in FIG. 7A, conditioned media from cells transfected with a plasmid encoding wild-type huHGF stimulated the incorporation of 3H in primary rat hepatocyte culture. As shown previously, the single-chain HGF variant R494E HGF and the protease domain variant Y673S,V692S HGF were defective in mitogenic activity (FIG. 7B). Interestingly however, the mitogenic activity of these variants was completely restored when expressed as an IgG fusion protein. Similarly, conditioned media from cells expressing the NK2-IgG variant (FIGS. 7A and 7B), the NK1-IgG variant (FIG. 7B) but not NK2 or NK1 alone (data not shown) also exhibited substantial mitogenic activity. The experiments also show that not all IgG fusion proteins act as hepatic mitogens because the CD4-IgG control failed to induce hepatocyte proliferation. This data are believed to indicate that fusion of the IgG heavy chain region to the HGF variants restores mitogenic activity by causing these variants to be expressed as dimers.

All citations cited throughout the specification, and the references cited therein, are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

I claim:

1. A method for recovering the biological activity of an inactive hepatocyte growth factor (HGF) variant which includes at least the Kringle 1 domain of native human HGF and selectively binds to an HGF receptor, comprising:

a) coupling two molecules of said inactive HGF variant to obtain a homodimer; or coupling said inactive HGF variant with a second HGF receptor binding amino acid sequence to obtain a heterodimer; and b) contacting said homodimer or heterodimer with at least two molecules of HGF receptor such that one molecule of said HGF variant binds to a first molecule of the HGF receptor and a second molecule of said HGF variant or said second receptor binding amino acid sequence binds to a second molecule of the HGF receptor wherein said binding results in biological activity.

2. The method of claim 1 wherein said coupled homodimer comprises two said HGF variants covalently fused to each other.

3. The method of claim 1 wherein said inactive HGF variant is an hHGF variant.

4. The method of claim 3 wherein said homodimer or heterodimer is coupled by a heterologous linker comprising an immunoglobulin.

\* \* \* \* \*